(12) United States Patent
Freschl et al.

(10) Patent No.: US 9,763,584 B2
(45) Date of Patent: *Sep. 19, 2017

(54) INTERMESHING LIGHT BARRIER FEATURES IN OPTICAL PHYSIOLOGICAL PARAMETER MEASUREMENT DEVICE

(71) Applicant: Fitbit, Inc., San Francisco, CA (US)

(72) Inventors: Daniel J. Freschl, Berkeley, CA (US); Chris H. Sarantos, San Francisco, CA (US); Peter W. Richards, San Francisco, CA (US); Anthony Alexander Cacace, San Francisco, CA (US); Ritika Sahai, Alameda, CA (US); Lindsey Michelle Sunden, San Francisco, CA (US)

(73) Assignee: Fitbit, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/194,543

(22) Filed: Jun. 27, 2016

(65) Prior Publication Data

US 2017/0086692 A1    Mar. 30, 2017

Related U.S. Application Data

(63) Continuation of application No. 15/183,687, filed on Jun. 15, 2016.
(Continued)

(51) Int. Cl.
*A61B 5/00* (2006.01)
*A61B 5/024* (2006.01)

(52) U.S. Cl.
CPC ...... *A61B 5/02433* (2013.01); *A61B 5/02438* (2013.01); *A61B 5/681* (2013.01);
(Continued)

(58) Field of Classification Search
CPC .............. A61B 5/02416; A61B 5/0205; A61B 5/02427; A61B 5/0245; A61B 5/0531;
(Continued)

(56) References Cited

U.S. PATENT DOCUMENTS

| 9,226,663 B2 * | 1/2016 | Fei ....................... A61B 5/0059 |
| 2005/0028482 A1 * | 2/2005 | Cable ................... A61B 5/0059 52/749.1 |

(Continued)

OTHER PUBLICATIONS

U.S. Office Action dated Nov. 16, 2016, in U.S. Appl. No. 15/194,504.
U.S. Office Action dated Dec. 15, 2016, in U.S. Appl. No. 15/183,687.
U.S. Restriction Requirement dated Sep. 30, 2016, in U.S. Appl. No. 15/183,687.

*Primary Examiner* — Christopher Cook
(74) *Attorney, Agent, or Firm* — Weaver Austin Villeneuve & Sampson LLP

(57) ABSTRACT

An optical measurement module is disclosed that includes three or more recessed regions separated from each other by two or more barrier walls, the recessed regions including at least two distal recessed regions. The optical measurement module may also include first and second photo-emitter elements that emit light in different spectrums and first and second photodetector elements. One or more of the second photo-emitter elements may be located in one of the distal recessed regions, and the second photodetector element may be located in one of the other distal recessed regions. The first photodetector element may be located in a recessed region other than the recessed region where the second photodetector element is located, and the one or more photo-emitter elements may be located in one of the recessed regions other than the one where the first photodetector element is located.

30 Claims, 34 Drawing Sheets

Related U.S. Application Data

(60) Provisional application No. 62/233,220, filed on Sep. 25, 2015, provisional application No. 62/279,584, filed on Jan. 15, 2016.

(52) U.S. Cl.
CPC ............... *A61B 2560/0462* (2013.01); *A61B 2562/0238* (2013.01); *A61B 2562/043* (2013.01)

(58) Field of Classification Search
CPC ..... A61B 5/0537; A61B 5/681; A61B 5/6824; A61B 5/6825; A61B 5/6831; A61B 5/7214; A61B 5/7225; A61B 5/7246; A61B 5/7435
See application file for complete search history.

(56) References Cited

U.S. PATENT DOCUMENTS

| | | | |
|---|---|---|---|
| 2013/0221380 A1* | 8/2013 | Ankireddi | H01L 25/0753 257/88 |
| 2014/0135631 A1* | 5/2014 | Brumback | A61B 5/02438 600/479 |
| 2016/0029911 A1* | 2/2016 | Lee | A61B 5/02427 600/301 |
| 2016/0287181 A1* | 10/2016 | Han | A61B 5/7214 |

* cited by examiner

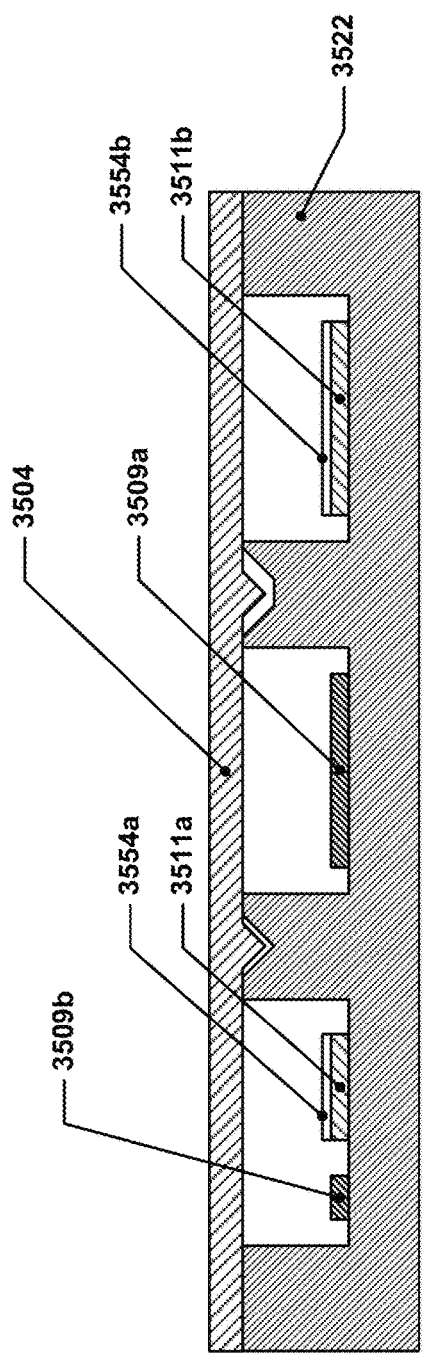
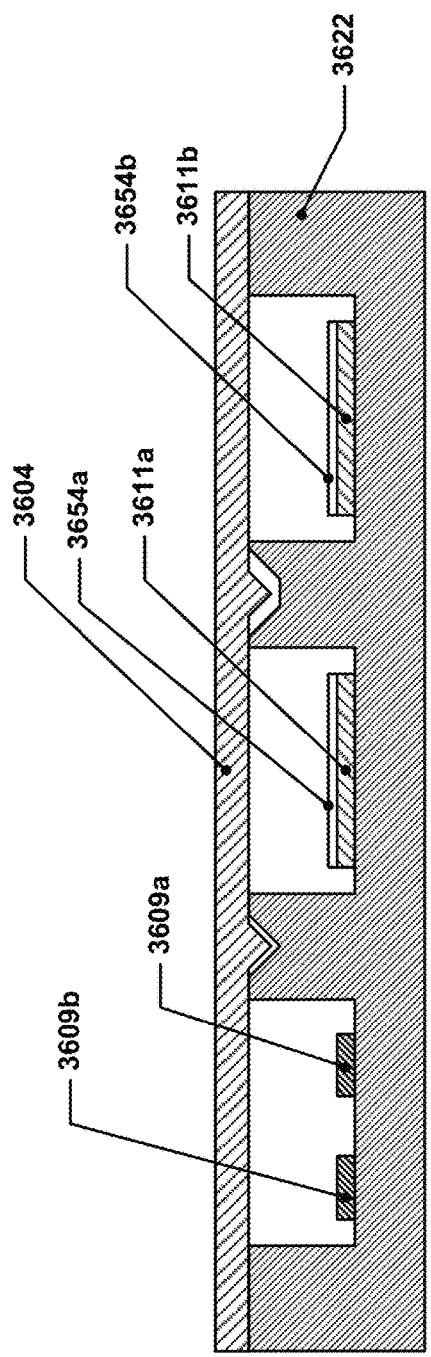

INTERMESHING LIGHT BARRIER FEATURES IN OPTICAL PHYSIOLOGICAL PARAMETER MEASUREMENT DEVICE

CROSS REFERENCE TO RELATED APPLICATIONS

This application claims priority under 35 U.S.C. §120 as a continuation application of U.S. patent application Ser. No. 15/183,687, filed Jun. 15, 2016, which, in turn, claims benefit of priority under 35 U.S.C. §119(e) to U.S. Provisional Patent Application Nos. 62/233,220, filed Sep. 25, 2015, and 62/279,584, filed Jan. 15, 2016, all of which are titled "INTERMESHING LIGHT BARRIER FEATURES IN OPTICAL PHYSIOLOGICAL PARAMETER MEASUREMENT DEVICE" and all of which are hereby incorporated herein by reference in their entireties.

BACKGROUND

Personal fitness and health monitoring devices, referred to as biometric monitoring devices herein, may include a variety of different sensors that are used to provide feedback regarding various physiological characteristics of a person. Such sensors may include, but are not limited to, accelerometers used to track activity intensity and steps taken, barometric pressure sensors used to track elevation gain, galvanic skin response sensors for detecting perspiration, and heart rate sensors that track heart rate and sometimes other physiological characteristics.

One type of sensor that may be used in biometric monitoring devices is an optical physiological parameter measurement device or sensor, such as a photoplethysmographic (PPG) heart rate sensor, that uses a photo-emitter and a photodetector. In a PPG sensor, a photo-emitter located adjacent to a person's skin emits light that is diffused within the person's skin and then reflected back out of the person's skin and into a photodetector. The amount of the emitted light that is diffused/reflected back out of the person's skin and into the photodetector will vary with the person's pulse rate. This is because the person's blood vessels will expand and contract in response to every heartbeat, e.g., as the heart pushes blood into the blood vessels, they expand—when the heart is no longer exerting pressure on the blood, the blood vessels contract. As the blood vessels expand and contract, the volume occupied by the blood vessels fluctuates, which affects the amount of light that is reflected back into the photodetector. This variation is cyclic and, by analyzing the amount of reflected light that is detected by the photo-emitter, it is possible to determine the frequency of that cyclic behavior and, therefore, the person's heart rate.

The concepts discussed herein may be applied to PPG sensors, as well as to other optical physiological parameter measurement devices, such as optically-based physiological sensors that utilize a light source coupled with a photodetector configured to detect light from the light source that is reflected off of a person's body or reflectively diffused from the person's body (such sensors may be classified as "reflective" sensors since they operate using light that is emitted and then reflected from a person's body); this disclosure is to be understood as not being limited to only PPG sensors or only PPG heart rate sensors. It is also to be understood that a PPG heart rate sensor is only one form of PPG sensor, and that other PPG sensors may measure other physiological parameters in place of, or in addition to, heart rate.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, an optical physiological parameter measurement apparatus may be provided. The optical physiological parameter measurement apparatus may include a photodetector element, a photo-emitter element, and a barrier wall interposed between the photo-emitter element and the photodetector element. The barrier wall may include one or more barrier wall surfaces. The optical physiological parameter measurement apparatus may also include a window and a protrusion that is attached to or part of the window. The protrusion may include one or more protrusion surfaces, and a subset of the one or more barrier wall surfaces and a subset of the one or more protrusion surfaces may define two surface profiles that intermesh with one another between the photo-emitter element and the photodetector element.

In some such implementations, the photo-emitter element may be the closest operable photo-emitter element to the photodetector element in the apparatus.

In some additional or alternative such implementations, the photo-emitter element may be configured such that 50% or more of the light emitted by the photo-emitter element is in the green wavelength spectrum. In some other implementations, the photo-emitter element may be configured such that 50% or more of the light emitted by the photo-emitter element is in the red or infrared wavelength spectra.

In some implementations of the optical physiological parameter measurement apparatus, the two surface profiles defined by the subset of the one or more barrier wall surfaces and the subset of the one or more protrusion surfaces may intermesh with one another such that any optical path originating at the photo-emitter element and reaching the photodetector element by travelling between the two surface profiles must strike at least one surface from the group consisting of the subset of the one or more barrier wall surfaces and the subset of the one or more protrusion surfaces before reaching the photodetector element.

In some implementations of the optical physiological parameter measurement apparatus, the two surface profiles defined by the subset of the one or more barrier wall surfaces and the subset of the one or more protrusion surfaces may intermesh with one another such that at least a first portion of a barrier wall surface in the subset of the one or more barrier wall surfaces is located closer to the window than at least a first portion of a protrusion surface in the subset of the one or more protrusion surfaces.

In some further such implementations of the optical physiological parameter measurement apparatus, at least a second portion of at least one of the one or more barrier wall surfaces may be located further from the window than at least a second portion of at least one of the one or more protrusion surfaces.

In some implementations of the optical physiological parameter measurement apparatus, the apparatus may further include a common substrate and the photodetector element and the photo-emitter element may both be mounted to the common substrate. In such an implementation, the barrier wall may extend away from the common substrate, and the two surface profiles defined by the subset of the one or more barrier wall surfaces and the subset of the one or more protrusion surfaces may intermesh with one another such that the barrier wall surfaces in the subset of the one or more barrier wall surfaces face towards the protrusion surfaces in the subset of the protrusion surfaces and the protrusion surfaces in the subset of the one or more protrusion surfaces face towards the barrier wall surfaces in the subset of the one or more barrier wall surfaces, at least one of the barrier wall surfaces in the subset of the one or more barrier wall surfaces is not parallel to the common substrate, and at least one of the protrusion surfaces in the subset of the one or more protrusion surfaces is not parallel to the common substrate.

In some implementations of the optical physiological parameter measurement apparatus, the photodetector element and the photo-emitter element may both be mounted to a first side of a common substrate and the barrier wall may extends away from the first side of the common substrate.

In some implementations of the optical physiological parameter measurement apparatus, the protrusion and the barrier wall may both be opaque to at least light in the green wavelength spectrum, either in the range of 495 to 570 nm or 500 to 600 nm.

In some implementations of the optical physiological parameter measurement apparatus, the protrusion and the window may both be made from plastic and the protrusion may be fused to the window.

In some implementations of the optical physiological parameter measurement apparatus, an edge of the photodetector element closest to the photo-emitter element may be offset from the center of the photo-emitter element by a distance of less than 2.6 mm.

In some implementations of the optical physiological parameter measurement apparatus, the barrier wall may be less than 1 mm thick as measured along an axis spanning between the photodetector element and the photo-emitter element.

In some implementations of the optical physiological parameter measurement apparatus, the subset of the one or more barrier wall surfaces may include two barrier wall surfaces forming a first angle between them, and the subset of one or more protrusion surfaces may include two protrusion surfaces forming a second angle within ±10° of the first angle.

In some implementations of the optical physiological parameter measurement apparatus, the subset of the one or more barrier wall surfaces may further include a third barrier wall surface extending away from one of the two barrier wall surfaces in a direction within ±10° of parallel with the window where the protrusion is located, and the subset of the one or more protrusion surfaces may include a third protrusion surface extending away from one of the two protrusion surfaces in a direction within ±10° of parallel with the window where the protrusion is located.

In some implementations of the optical physiological parameter measurement apparatus, the subset of barrier wall surfaces may include a barrier wall surface that is sloped such that that barrier wall surface approaches the window as that barrier wall surface is traversed from an end of that barrier wall surface closest to the photodetector element to an end of that barrier wall surface closest to the photo-emitter element. In some such implementations, the subset of the one or more barrier wall surfaces may include a single barrier wall surface.

In some implementations of the optical physiological parameter measurement apparatus, the subset of the one or more barrier wall surfaces may include at least two barrier wall surfaces and one of the two barrier wall surfaces extends in a direction within ±10° of parallel with the window where the protrusion is located.

In some implementations of the optical physiological parameter measurement apparatus, the subset of the one or more barrier wall surfaces and the subset of the one or more protrusion surfaces may have complementary profiles.

In some implementations of the optical physiological parameter measurement apparatus, at least one barrier wall surface in the subset of the one or more barrier wall surfaces may be offset from a corresponding protrusion surface in the subset of the one or more protrusion surfaces by between 0 mm and 0.5 mm.

In some implementations of the optical physiological parameter measurement apparatus, the subset of the one or more barrier wall surfaces may include at least three barrier wall surfaces that are each within ±10° of perpendicular to each adjacent barrier wall surface.

In some implementations, an optical physiological parameter measurement apparatus may be provided. The optical physiological parameter measurement apparatus may include, for example, a photoplethysmographic (PPG) sensor module including a photodetector and a photo-emitter, wherein the PPG sensor module may include a barrier wall interposed between the photo-emitter and the photodetector, and a window having a plurality of window surfaces on a side of the window facing towards the photo-emitter and the photodetector. A subset of the one or more window surfaces may define a groove that at least partially overlaps the barrier wall when viewed along an axis perpendicular to the window and passing through the barrier wall. Moreover, the barrier wall may include one or more barrier wall surfaces and a subset of the one or more barrier wall surfaces faces towards the window surfaces in the subset of the one or more window surfaces, and the subset of the one or more barrier wall surfaces may protrude into the groove such that any light traveling from a side of the barrier wall facing the photo-emitter to a side of the barrier wall facing the photodetector and in between the subset of the one or more barrier wall surfaces and the subset of the one or more window surfaces must strike at least one surface selected from the group consisting of the subset of the one or more barrier wall surfaces, the subset of the one or more window surfaces, and the subsets of the one or more barrier wall surfaces and the one or more window surfaces before reaching the side of the barrier wall facing the photodetector.

In some implementations of the optical physiological parameter measurement apparatus, the barrier wall may be opaque to at least light in the green wavelength spectrum selected from the group of ranges consisting of: 495 to 570 nm, 500 to 600 nm, and 495 to 600 nm.

In some implementations of the optical physiological parameter measurement apparatus, the window may have an exterior surface facing in an opposite direction from the surface having the groove, and the exterior surface may not have any discontinuities in areas corresponding with the location of the groove.

In some implementations of the optical physiological parameter measurement apparatus, the window may have an exterior surface facing in an opposite direction from the surface having the groove, and the exterior surface in areas corresponding with the location of the groove may have a protrusion that causes the thickness of the window at a deepest part of the groove to be greater than the thickness of the window at a location other than the groove minus the depth of the groove at the deepest part of the groove.

In some implementations of the optical physiological parameter measurement apparatus, the subset of the one or more barrier wall surfaces and the subset of the one or more window surfaces may have complementary profiles.

In some implementations of the optical physiological parameter measurement apparatus, each barrier wall surface in the subset of the one or more barrier wall surfaces may be offset from a corresponding window surface in the subset of the one or more window surfaces by 0 mm and 0.5 mm.

In some implementations, an optical physiological parameter measurement apparatus may be provided that includes a common substrate, a photodetector element mounted to a first side of the common substrate, a photo-emitter element mounted to the first side of the common substrate, a barrier wall interposed between the photodetector element and the photo-emitter element and extending away from the first side of the common substrate. The barrier wall may have a first side facing towards the photodetector element, a second side facing towards the photo-emitter element, and one or more surfaces interposed between the first side of the barrier wall and the second side of the barrier wall, and at least one of the one or more surfaces may not be parallel to the common substrate.

In some implementations of the optical physiological parameter measurement apparatus, the one or more surfaces may form a V-shaped groove.

In some implementations of the optical physiological parameter measurement apparatus, the one or more surfaces may include at least one surface that extends from an edge of the V-shaped groove in a direction parallel to the common substrate.

In some implementations of the optical physiological parameter measurement apparatus, the apparatus may include a perimeter wall that encircles the photodetector element and the photo-emitter element, and the barrier wall may extend from one portion of the perimeter wall to another portion of the perimeter wall.

In some implementations, a method may be provided. The method may include providing an optical physiological parameter measurement sensor module including a photo-emitter element, a photodetector element, and a barrier wall interposed between the photo-emitter element and the photodetector element, the barrier wall including one or more barrier wall surfaces. The method may further include providing a window that includes a protrusion that is attached to or part of the window, the protrusion including one or more protrusion surfaces, positioning the window and the optical physiological parameter measurement sensor module relative to one another such that a subset of the one or more barrier wall surfaces defining a first surface profile and a subset of the one or more protrusion surfaces defining a second surface profile intermesh with one another between the photo-emitter element and the photodetector element, and fixing the window and the optical physiological parameter measurement sensor module in place relative to one another.

In some implementations of the method, the window and the optical physiological parameter measurement sensor module may be positioned relative to one another such that any optical path originating at the photo-emitter element and reaching the photodetector element by travelling between the first surface profile and the second surface profile must strike at least one surface from the group consisting of the subset of the one or more barrier wall surfaces and the subset of the one or more protrusion surfaces before reaching the photodetector element.

In some implementations, an optical physiological parameter measurement apparatus may be provided that has an optical measurement module having three or more recessed regions arranged side-by-side and separated from each other by two or more barrier walls, the recessed regions including at least two distal recessed regions. The optical physiological parameter measurement apparatus may have one or more first photo-emitters that are configured to emit light predominantly in the green light spectrum and one or more second photo-emitters that are configured to emit light predominantly in the red to infrared light spectrum. The optical physiological parameter measurement apparatus may also have a first photodetector and a second photodetector. The one or more second photo-emitters may be located in one of the distal recesses, the second photodetector may be located in one of the other distal recesses, the first photodetector may be located in one of the recesses other than the distal recess that the second photodetector is located in, and the one or more first photo-emitters may be located in one of the recesses other than the recess that the first photodetector is located in.

In some such implementations of the optical physiological parameter measurement apparatus, the first photodetector may be located in the same distal recess as the one or more second photo-emitter elements, and the one or more first photo-emitter elements may be located in a recess between the recesses in which the one or more second photo-emitter elements and the second photodetector element are located.

In some other implementations, the one or more first photo-emitter elements and the one or more second photo-emitter elements may be located in a common one of the recesses and the first photodetector element may be located in a recess in between the recesses in which the one or more first photo-emitter elements and the second photodetector element are located.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIG. 35 is a schematic diagram of an OMM with two different optical physiological parameter measurement devices.

FIG. 36 is a schematic diagram of another OMM with two different optical physiological parameter measurement devices.

DETAILED DESCRIPTION

Figure 1:
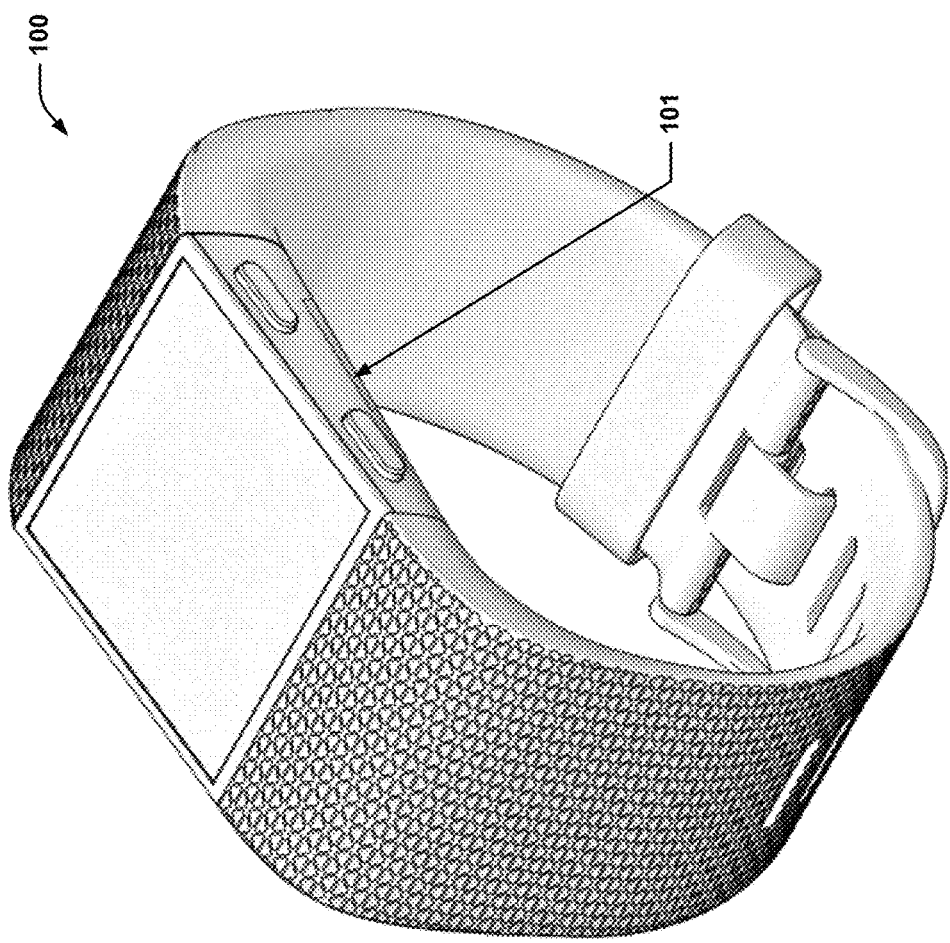
FIG. 1 depicts an example of a biometric monitoring device.

FIG. 1 depicts an example of a biometric monitoring device. As shown, the biometric monitoring device 100 takes the form of a wristwatch, similar to the Fitbit™ Surge™, although the concepts discussed herein may be applied to other form factors, such as a pendant-, ring-, or pager-style form factors, of biometric monitoring devices, as well as to devices that may have biometric monitoring capabilities built-in, such as smartphones, tablets, game controllers, television controllers, or any other suitable electronic device or computer. The biometric monitoring device 100 may have a subsection 101 that faces a person's skin when worn or used; this subsection 101 may include an optical heart rate sensor, blood oxygen saturation sensor, respiration sensor, or other optical physiological sensor involving a light source and a photodetector. The subsection 101 may include a portion of a device housing and a window. The device housing may be made from injection molded plastic, metal, or other material, and may typically be optically opaque. The device housing may also be made using techniques other than injection molding, if desired, although injection molding or similar molding processes may be the most cost-effective avenue for mass-production.

Figure 2:
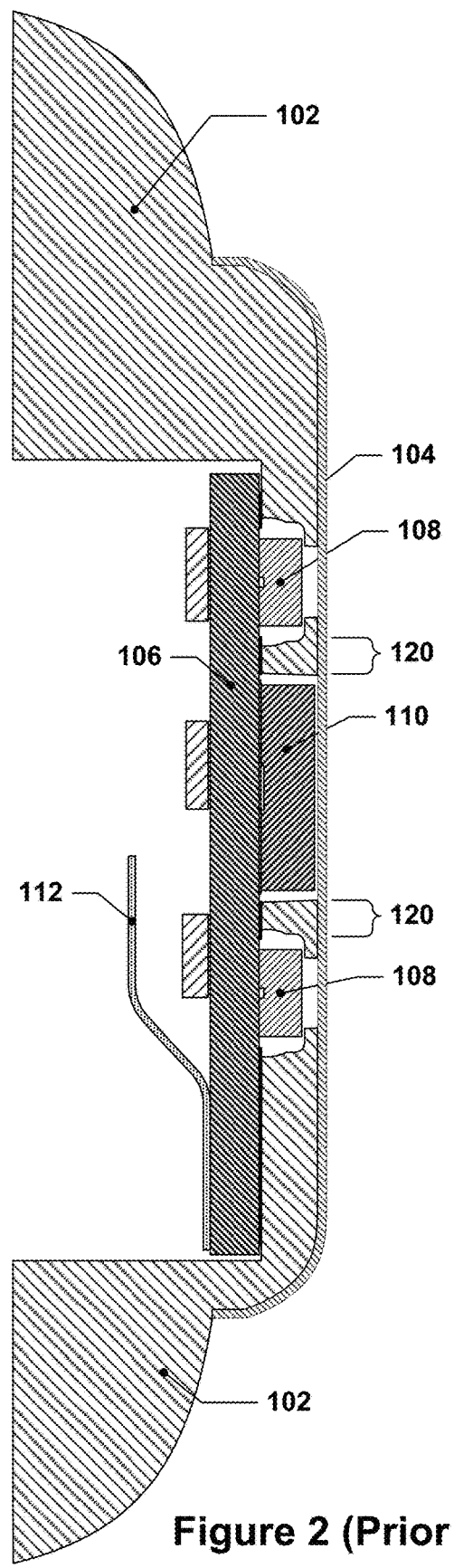
FIG. 2 depicts a removed section view of the subsection of FIG. 1.
Figure 3:
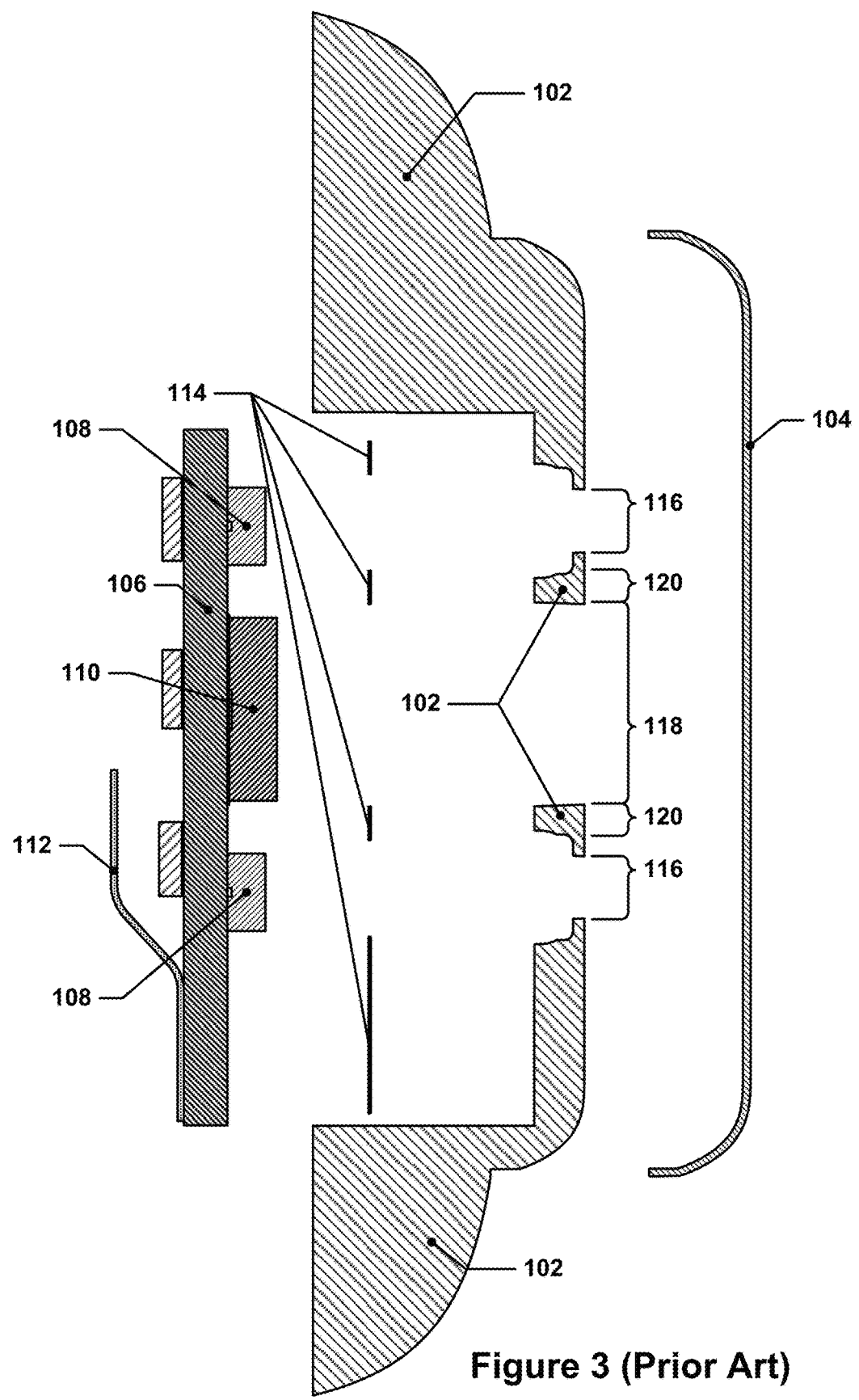
FIG. 3 depicts an exploded view of the removed section of FIG. 2.

FIG. 2 depicts a removed section view of the subsection 101 of FIG. 1. FIG. 3 depicts an exploded view of FIG. 2. These section views are taken through a plane that passes through the middle of the subsection 101 and that is generally parallel to the forearm axis of a person wearing the biometric monitoring device 100.

As can be seen, the subsection 101 may include a portion of a device housing 102, as well as a window 104. The window 104 may be made from a material that is optically transparent, or that is at least optically transparent to the wavelengths of light used in the optical heart rate sensor. For example, it is common to use photo-emitters that emit light in the green light spectrum for optical heart rate sensors, as light of these wavelengths exhibits a greater degree of intensity modulation in response to traveling through blood and the fluctuations in such light due to arterial expansion/contraction are thus easier to detect. Accordingly, the window 104 may be made from a material that is optically transparent to green light but that is perhaps optically opaque to light of other wavelengths, e.g., red light. Such a window, for example, may be transparent to green light in the 495 to 570 nm wavelength, 500 to 600 nm, or 495 to 60 nm wavelength ranges. If other types of optical physiological sensors are used instead of or in addition to an optical heart rate sensor, then the window may be tailored to be optically transparent for those other wavelengths of light as well, such as wavelengths for red, yellow, or infrared light.

In some implementations, the window 104 may be a component that is non-destructively separable from the device housing 102, but in other implementations, the window 104 may be fused or permanently adhered to the device housing 102. For example, in some implementations, the window 104 may be formed using an injection molding or thermomolding process, and then placed into the mold cavity that is used to produce the device housing 102. When the molten plastic that is used to form the device housing 102 is then injected into the mold cavity, it flows against the window 104 and then fuses to the window 104 when it cools. The mold cavity may be designed such that portions of the device housing 102 may form apertures or openings, such as photo-emitter apertures 116 and photodetector aperture 118, where there is no device housing material adjacent to the window 104. The fused window/device housing interface may thus provide a hermetic seal between the window 104 and the device housing 102, while still allowing light to pass through portions of the window 104 overlaying any apertures or openings in the device housing 102.

Also visible in FIGS. 2 and 3 are photo-emitters 108 and a photodetector 110. These elements may be mounted to a printed circuit board (PCB) 106, which may be connected to other electronic elements of the biometric monitoring device 100 by a cable 112. The PCB 106 may be mounted to the back side of the device housing 102 such that the photo-emitters 108 are aligned with the photo-emitter apertures 116 and the photodetector 110 is aligned with the photodetector aperture 118.

The PCB may be held in place by, for example, a screw or other fastener system, or by other mechanisms, such as by melting one or more plastic pins that protrude from the device housing and pass through holes on the PCB 106 such that the plastic pins "mushroom" and, when cooled, positively engage with the PCB 106 to prevent the PCB 106 from pulling away from the device housing 102. Other methods of holding the PCB 106 in place may also be used, such as snap-in clips, adhesives, etc.

As can be seen, the device housing 102 forms two walls 120 that extend from the window 104 towards the PCB 106. These walls 120 serve to prevent light from the photo-emitters 108 from reaching the photodetector 110 without first travelling through the window 104. In such a configuration, the PCB 106 may have a layer of double-sided adhesive tape 114 that may be used to help locate the PCB 106 in place relative to the device housing 102 during assembly. As can be seen, the implementation depicted in FIGS. 2 and 3 generally prevents light emitted by the photo-emitters 108 from reaching the photodetector 110 without first exiting the device housing 102 via the window 104.

The implementations shown in FIGS. 2 and 3 utilize a heart rate sensor that is built from discrete components assembled to the PCB 106. Biometric monitoring device manufacturers, in the past, typically manufactured such heart rate sensors in such a manner, although the limitations of available piece-part components generally limited the degree to which such sensors could be miniaturized. For example, the photo-emitters 108 may, in some example biometric monitoring devices, have a diameter of ~1.75 mm, and the photodetector 110 may be over 4 mm on a side. As a result, a heart rate sensor such as that implemented in FIGS. 2 and 3 may measure 14 mm or more along the long axis.

The present inventors have determined that there are advantages to using a single, integrated optical measurement module (OMM) that contains the photodetector(s) and photo-emitter(s) for an optical heart rate sensor in an integrated package instead of building such an optical heart rate sensor out of piece-parts. Examples of such OMMs include OSRAM Optical Semiconductors™, models SFH 7050™ (which includes photo-emitters of three different wavelengths suited for heart rate measurement, blood oxygen measurement, and proximity detection), SFH 7051™ (which is similar to the SFH 7050 but includes three green photo-emitters for heart rate measurement only), and the SFH 7060™ (which is a larger package that includes three green photo-emitters for heart rate measurement as well as red and infrared photo-emitters for blood oxygen measurement and proximity detection). Since OMMs are supplied as a single, integrated electronics package, biometric monitoring device manufacturers no longer have to assemble a heart rate sensor from scratch. Moreover, since OMMs are typically built by semiconductor manufacturers, they are able to be manufactured on a much smaller scale than is possible using commercial off-the-shelf PCB-board mount components. For example, the OSRAM™ models SFH 7050 and 7051 both measure 4.7 mm long, 2.5 mm wide, and 0.9 mm deep, i.e., nearly an entire OMM may fit within the volume occupied by the photodetector 110 used in some existing designs. The SFH 7060™ has the same form factor, except that the length is 7.2 mm instead of 4.7 mm.

Figure 4:
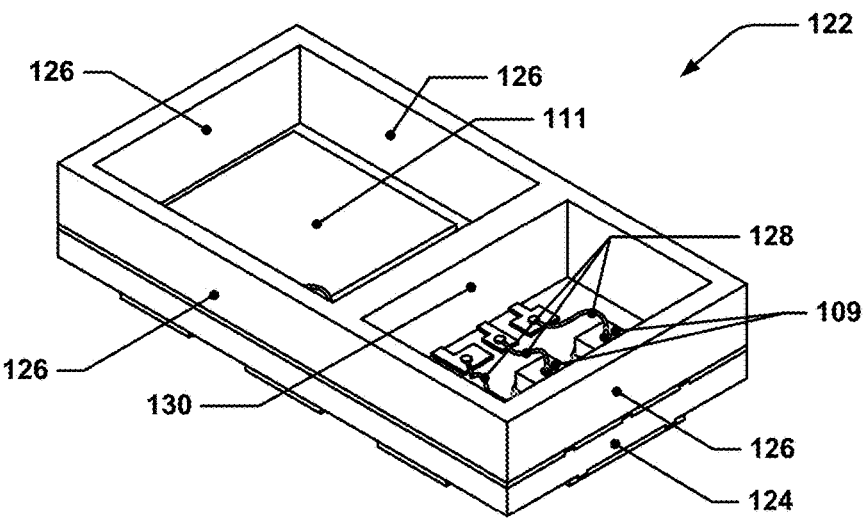
FIG. 4 depicts an isometric view of an example optical measurement module (OMM).
Figure 5:
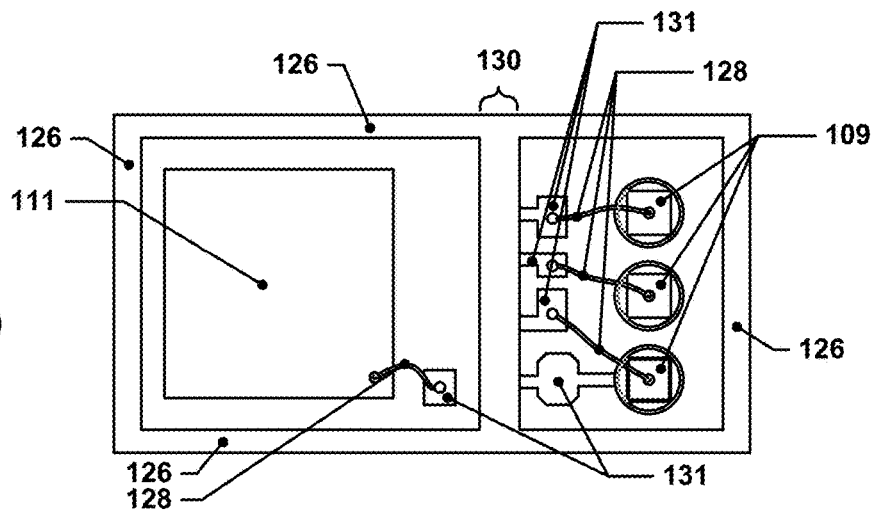
FIG. 5 depicts a plan view of the example OMM of FIG. 4.
Figure 6:
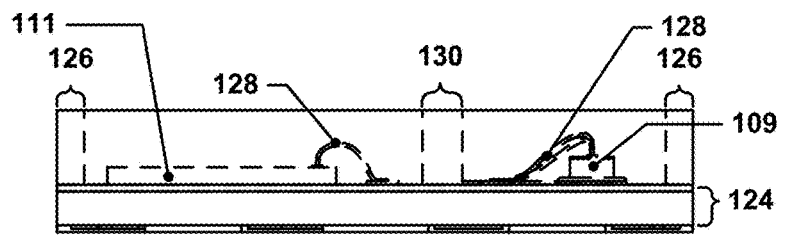
FIG. 6 depicts a side view of the example OMM of FIG. 4.
Figure 7:
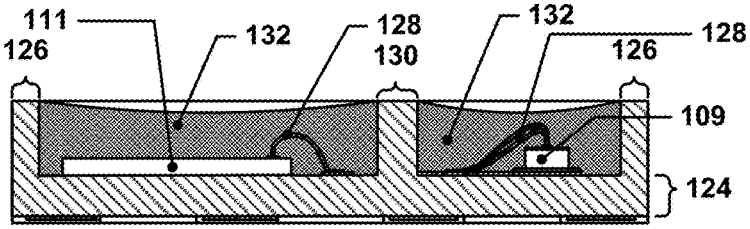
FIG. 7 depicts a side section view of the example OMM of FIG. 4.

FIG. 4 depicts an isometric view of an example optical measurement module (OMM). FIG. 5 depicts a plan view of the example OMM of FIG. 4. FIG. 6 depicts a side view of the example OMM of FIG. 4. FIG. 7 depicts a side section view of the example OMM of FIG. 4. The OMM 122 shown is based on the OSRAM™ SFH 7050™, although the discussion below is to be understood as not being limited to only such an OMM and may be equally applicable to other OMMs, including OMMs provided by other manufacturers. The OMM 122 may have a substrate 124 that includes circuit traces, such as circuit traces 131, that provide electrical connections between solder pads on the underside of the substrate 124 and electronic components within the OMM 122. Such electronic components may include, for example, photo-emitter elements 109 and photodetector element 111. In some cases, some of the electronic components may be connected with the circuit traces 131 by bond wires 128, although other mechanisms for establishing such electrical interconnects may be used in place of, or in addition to, such connections.

The OMM may, as with most electronic packages, be encapsulated in a hard plastic or resin in order to protect the components within from damage during handling and after installation. Unlike most semiconductor packages in which the only exposed portions of the circuit are the solder contact pads used to establish electrical connections with the circuitry that is embedded within the semiconductor package, OMMs typically need to allow for various circuit elements in the OMM semiconductor package to have optical paths through the encapsulant. In order to provide such optical paths, an OMM 122 may be encapsulated in an encapsulant that forms a perimeter wall 126 around the perimeter of the OMM but that is open at the "top" of the OMM 122 so as not to block light from reaching the photodetector element 111 or being emitted out of the OMM 122 by the photo-emitter elements 109. The OMM may also have an optically opaque barrier wall 130 that spans between portions of the perimeter wall 126 and that optically isolates the photo-emitter elements 109 from the photodetector element 111 within the OMM 122. The barrier wall 130 may be quite small, e.g., on the order of several tenths of a millimeter in width (for example, in a 4.7 mm long OMM package having the proportions shown in FIGS. 4 through 7, the barrier wall may be 0.3 mm in width). While not shown in FIGS. 4 through 6, the recesses formed by the perimeter walls 126 and the barrier wall 130 may be filled with a flowable encapsulant 132 that is optically transmissive. The encapsulant 132 may protect the photodetector element 111 and photo-emitter elements 109 from damage, e.g., from moisture or physical contact, while still providing an optical transmission path.

The present inventors have determined that it is desirable to place an OMM behind a transparent window in a biometric monitoring device, even if the OMM itself includes an optically transparent encapsulant, such as is described with respect to the example in FIG. 7. If no window is used with an OMM, then an unencapsulated OMM may be exposed to moisture, e.g., sweat from a person's skin, and suffer corrosion, not to mention become clogged with dirt and particulates, e.g., dead skin cells. If the OMM is encapsulated, this may prevent direct damage to the OMM but the seam between the OMM and the surrounding housing must still be sealed against moisture and dirt to avoid such contaminants from reaching the electronic connections on the back side of the OMM. Moreover, if an encapsulated OMM is allowed to be in direct contact with a person's skin, there is a risk that the encapsulant, which may be, for example, an epoxy, may cause an allergic response in the wearer's skin, leading to potential injury and discomfort.

Since a typical OMM will have a flat upper surface, i.e., the surface of the OMM through which light enters and exits the OMM, a heart rate sensor may be designed such that the OMM is placed such that the top surface of the OMM is flush against the interior surface of such a window. The present inventors have determined, however, that due to the fact that many OMMs are very small, e.g., less than 0.5 cm in largest dimension, it is difficult or impossible, from the manufacturing feasibility standpoint, to ensure that the top surface of the OMM will actually be in intimate contact with the interior surface of the window. Given the small width of the barrier wall in an OMM, even a very slight gap between the OMM top surface and the window interior surface may provide a light leakage path between the photo-emitters and the photodetector of the OMM. Such a gap may, for example, range from between 0 and 0.5 mm, depending on the tolerances selected. This issue is discussed further with reference to the following Figures.

Figure 8:
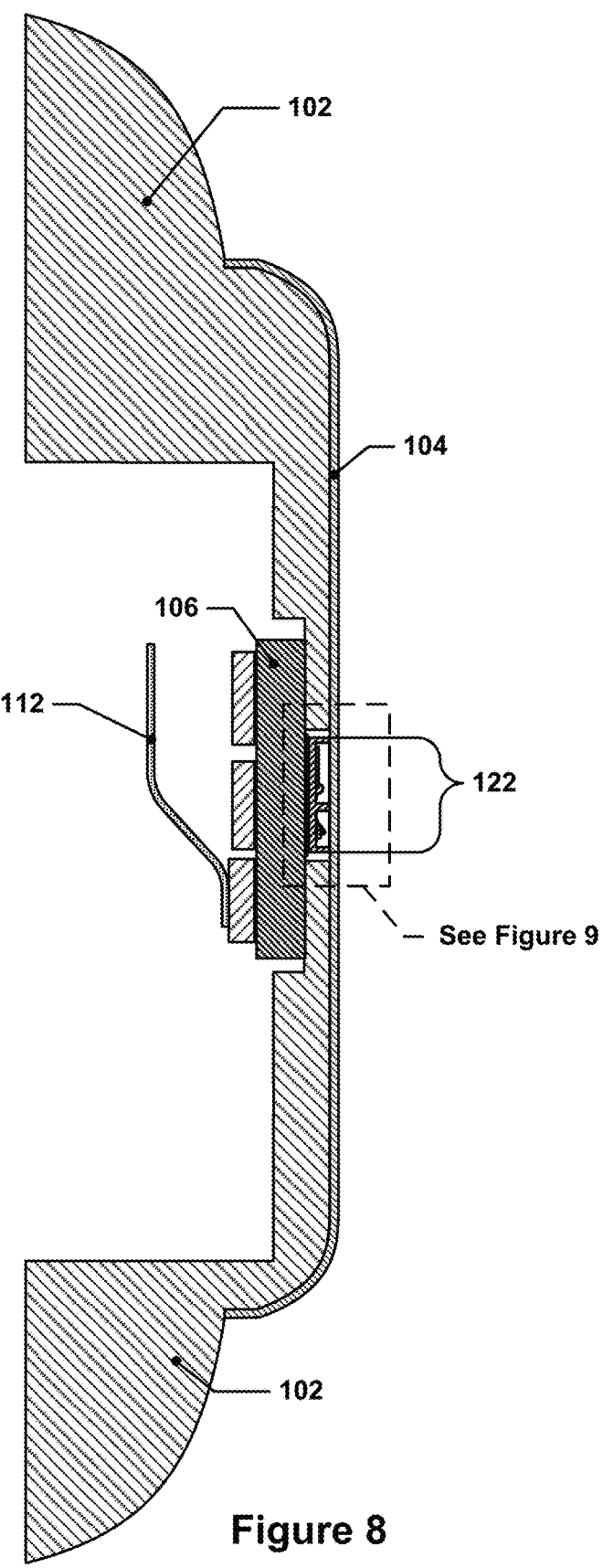
FIG. 8 depicts a removed section view of a subsection of a biometric monitoring device having an example OMM.
Figure 9:
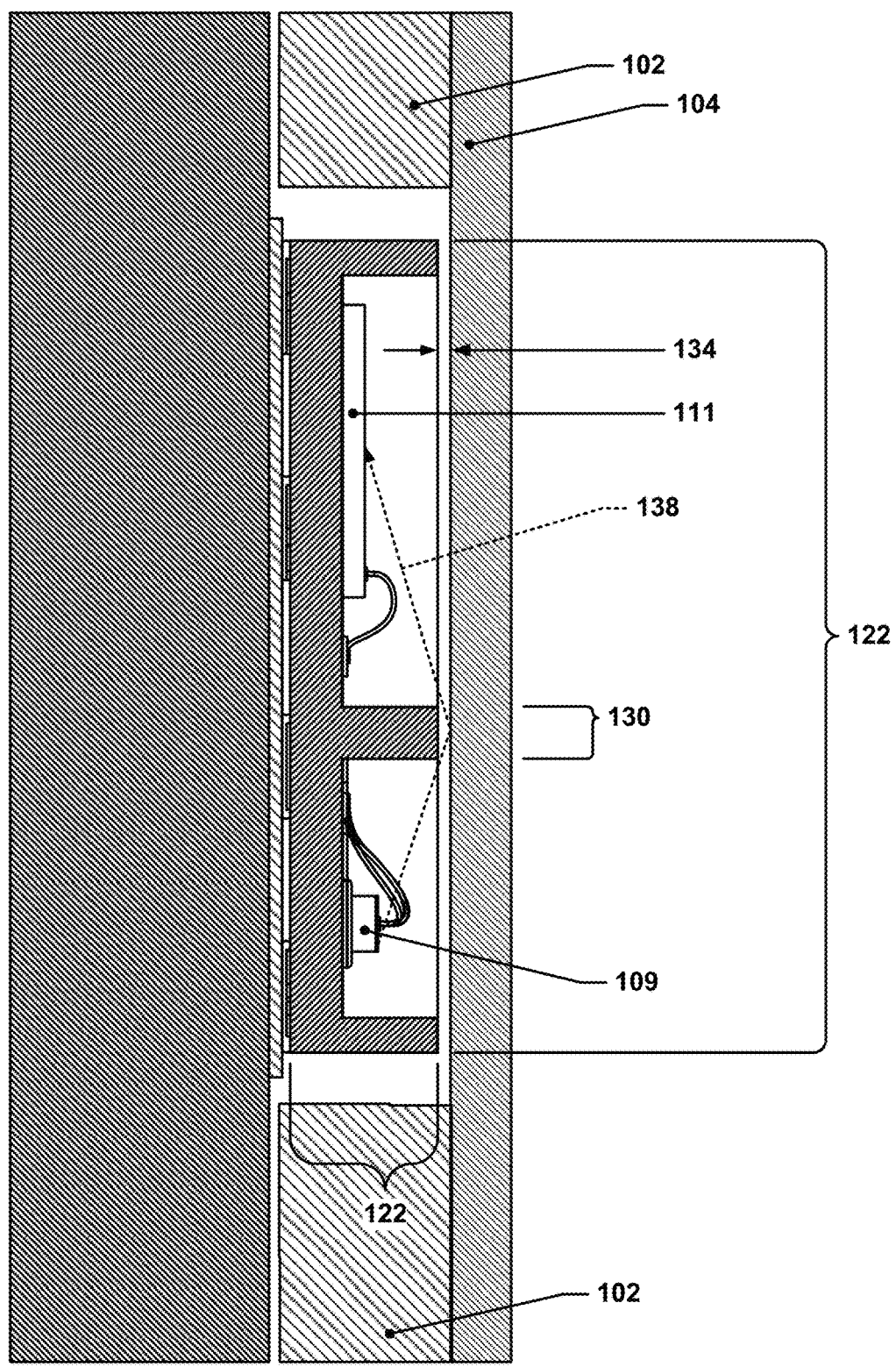
FIG. 9 is a detail view of the portion of FIG. 8 enclosed in a dashed rectangle.

FIG. 8 depicts a removed section view of a subsection of a biometric monitoring device having an example OMM. FIG. 9 is a detail view of the portion of FIG. 8 enclosed in a dashed rectangle.

In FIG. 8, a device housing 102 is shown with a window 104 attached thereto. A PCB 106 with a cable 112 is mounted to the device housing 102 as well. The PCB 106 has an OMM 122 mounted to it and in communicative electrical contact with the cable 112. For comparison's sake, the components in FIG. 8 are drawn to the same scale as the components in FIG. 2.

FIG. 9 depicts a detail view of the portion of FIG. 8 enclosed in a dashed rectangle. As can be seen, the device housing 102 has a window 104 that is connected to or fused with the device housing 102. The PCB 106 may be attached to the device housing 102 through any suitable connection; in this example, a double-sided adhesive tape 114 or other adhesive is used to hold the PCB 106 in place relative to the device housing 102 and the window 104. The OMM 122 may be soldered to the PCB 106 and may include one or more photo-emitter elements 109 and one or more photo-detector elements 111. A barrier wall 130 may separate the photo-emitter element(s) 109 from the photodetector element(s) 111.

The present inventors, however, determined that due to various assembly considerations, e.g., variability in the thickness of the solder joint between the OMM 122 and the PCB 106, variability in the thickness of the OMM 122 itself, variability in the thickness of the device housing 102, variability in offset distance between the PCB 106 and the device housing 102 due to the assembly technique or technology used to assemble such components, that it would be extremely difficult to mount an OMM 122 in such a device such that the top surface of the OMM 122 would always be in flush contact with the interior surface of the window 104 if such a device were to be mass-produced. Given these sources of variability, the top surface of the OMM 122 and the interior surface of the window 104 would generally be separated by a tolerance gap 134, which may amount, for example, to at least 0.1 mm or less. As can be seen, such a gap may allow light traveling from a photo-emitter element 109 along an optical path, such as optical path 138, to enter the gap between the top of the barrier wall 130 and the interior surface of the window 104 and then reflect off of the window 104 and strike the photodetector element 111. While some of the reflected light may be absorbed by or transmitted through the window 104, a large fraction of the light reflected off of the interior surface of the window 104 may be reflected and may reach the photodetector element 111. Such light, which has not been modulated by first passing through a person's skin, may have a much higher intensity than the light that has been modulated by passing through the person's skin, and may thus saturate the photodetector and wash out the modulated light, which may make it difficult or impossible to obtain a reliable heart rate signal.

Figure 10:
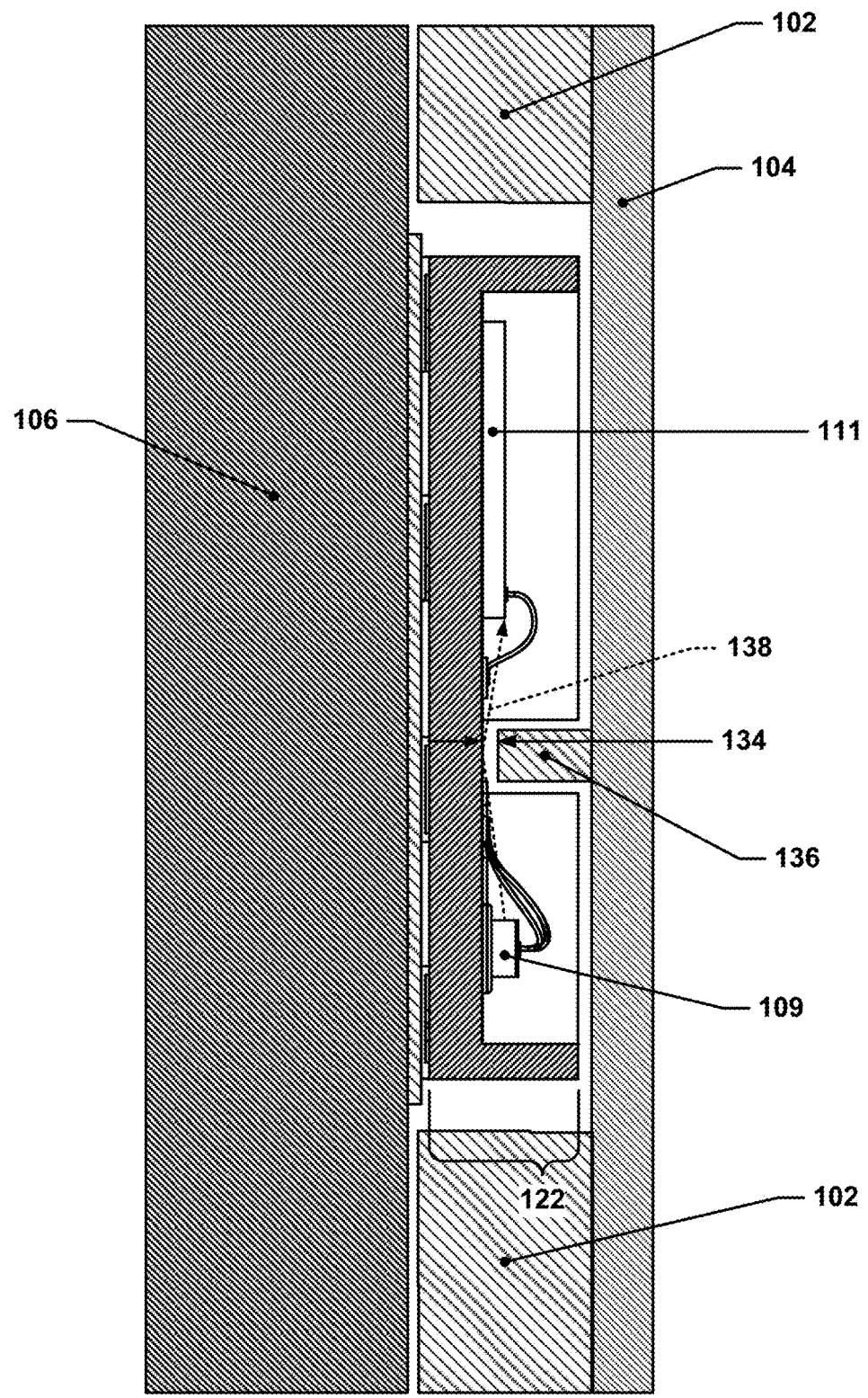
FIG. 10 depicts an alternate configuration for using an OMM in a biometric monitoring device.

A potential work-around to this issue conceived of by the inventors is to use an OMM without ant barrier wall and to include a protrusion that extends from the window 104 towards the substrate of the OMM. The perimeter wall of the OMM may have gaps in it where the protrusion exists, or the protrusion may be sized to have width that fits between the perimeter walls of the OMM. FIG. 10 depicts such an alternate approach. In FIG. 10, a protrusion 136, which may be part of the device housing 102, extends from the window 104 towards the substrate of the OMM 122. However, the inventors observed that this approach may encounter the same tolerance issues discussed above with respect to the implementation of FIG. 9. For example, the assembly tolerance stack-up may result in a tolerance gap 134 between the substrate of the OMM 122 and the protrusion 136; this tolerance gap 134 may range from between 0 and 0.5 mm. Light from the photo-emitter element 109 may, instead of reflecting off of the window 104 within the tolerance gap 134, reflect off of the substrate of the OMM 122 and reach the photodetector element 111, which may cause the same issues noted above.

Figure 11:
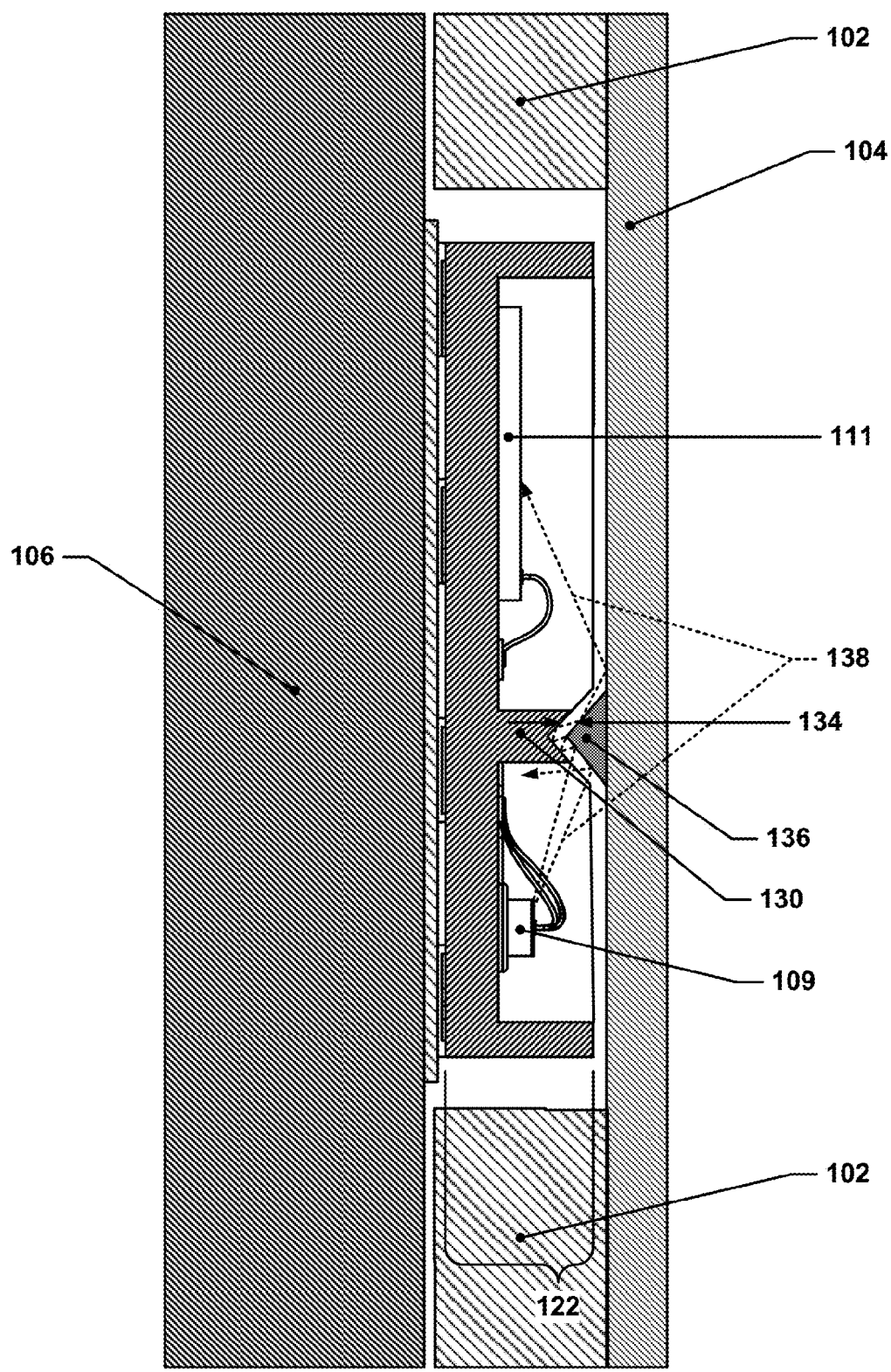
FIG. 11 depicts an implementation in which an OMM is used in a biometric monitoring device in conjunction with interlocking or intermeshing barrier wall and protrusion surface profiles.

The present inventors next conceived of a two-piece barrier design that included a barrier wall that extends from the substrate of the OMM 122 (or other structure supporting the photodetetector element 111 and the photo-emitter elements 109) towards the window 104, and a protrusion that extends from the window 104 towards the OMM 122. FIG. 11 depicts an implementation in which an OMM is used in a biometric monitoring device in conjunction with interlocking or intermeshing surface profiles of barrier wall and protrusion features. In this example, the OMM 122 has a barrier wall 130 where the surfaces facing towards the window 104 define a V-shaped groove. The window 104, correspondingly, has a protrusion 136 in the form of a triangular prism that is positioned such that the protrusion 136 intermeshes or interlocks with the V-shaped groove of the barrier wall 130. While there may still be a tolerance gap 134 that exists between the protrusion 136 and the barrier wall 130, the intermeshing or interlocking nature of the protrusion and the barrier wall surface profiles makes it impossible for a direct optical path to exist from the side of the barrier wall facing the photo-emitter elements 109 to the side of the barrier wall facing the photodetector element 111. The intermeshing or interlocking nature of the surface profiles of the protrusion and the barrier wall features also prevents light from the photo-emitter elements 109 from reaching the photodetector element 111 without first reflecting off of more than a single surface, e.g., any light from the photo-emitter elements 109 that reaches the photodetector element 111 without first exiting through the window 104 must reflect multiple times off of the surfaces of the barrier wall 130 or the protrusion 136. Each time such light reflects off of one of these surfaces, the intensity of the light is reduced, thereby reducing the impact that such internally reflected light may have on the photodetector element's ability to detect fluctuations in the light that is diffused/reflected back into the photodetector element 111 from a person's skin.

FIGS. 12 through 25 depict various implementations of barrier walls and protrusions with interlocking or intermeshing surface profiles in the context of an OMM. It is to be understood that two surface profiles forming the ends of the barrier wall and the protrusion "intermesh" or "interlock," as used herein, with each other when the combination of the two surface profiles limits the amount of light emitted from the photo-emitters that may reach the photodetector without first striking at least one surface of either the end of the barrier wall, the end of the protrusion, or both. In some cases, the surface profiles formed by the protrusion and the barrier wall include at least one surface that is not parallel to the window at the location of the protrusion. In the event that the window is not a planar window, it is to be understood that parallelism to the window refers to whether or not the surface in question is parallel to the planar average surface of the window For convenience, a legend is provided in the Figures that indicates, for each of FIGS. 12 through 25, the cross-hatching or patterning applied to each component in FIGS. 12 through 25. Thus, for example, the transparent window 104 in each of these Figures is represented by the component having the pattern shown in the legend. The exception to this convention is the barrier wall 130, which is separately called out using a bracket identifier in each Figure. It is to be understood that while the depicted implementations in FIGS. 12 through 25 do not show an encapsulant, the cavities in the OMM 122 in which the photo-emitter element 109 and the photodetector element 111 reside may be filled or partially filled with such a material to better protect these components. It is to be understood that used of relative directional terms such as "left," "right," "above," "on top of," "underneath," "below," etc. with reference to these Figures refers to the orientation of components with respect to the Figure orientation and should not be viewed as conveying any actual absolute orientation of components.

Figure 12:
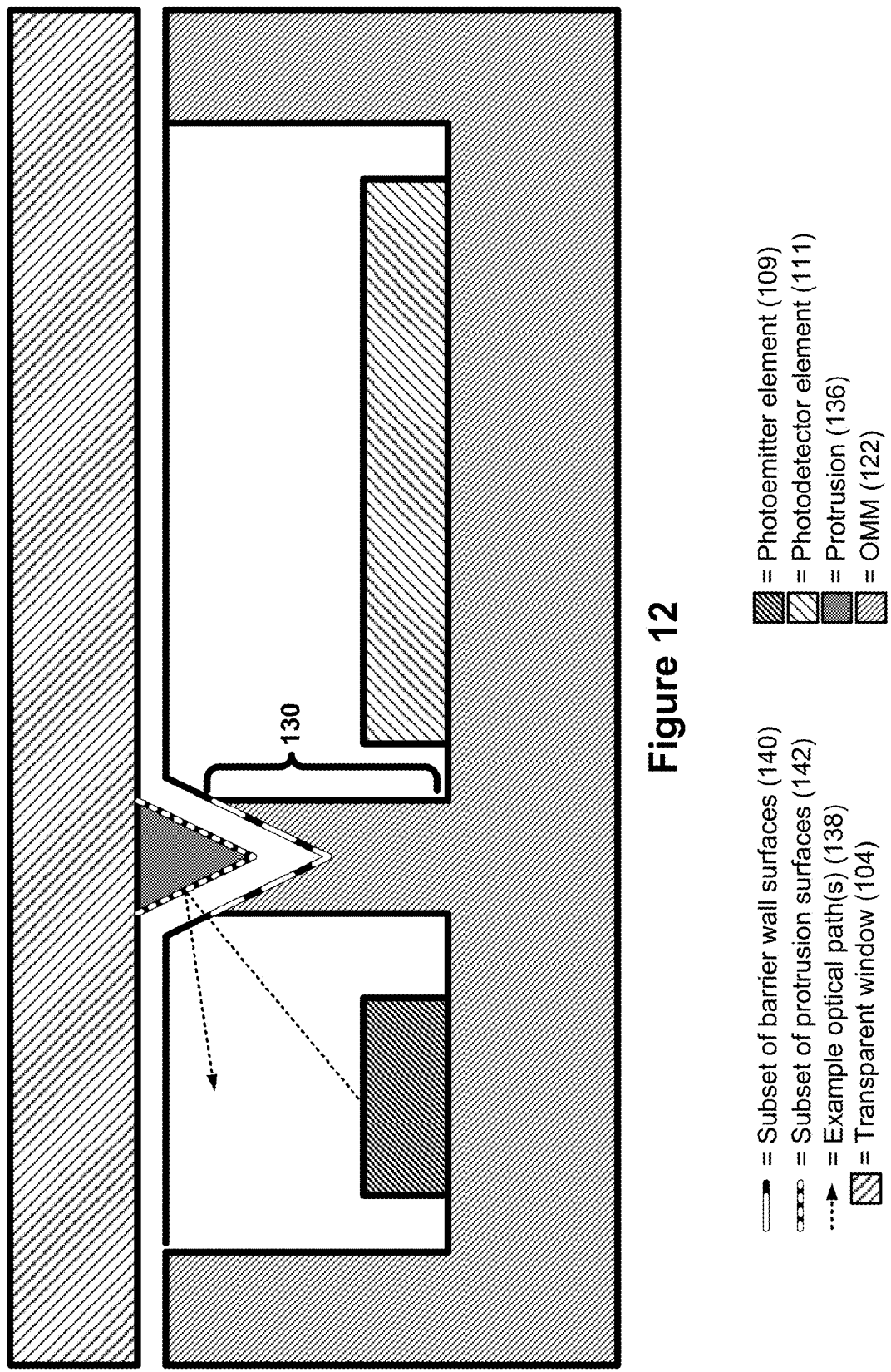
FIG. 12 depicts an example of a barrier wall and protrusion with interlocking or intermeshing surface profiles in the context of an OMM.

FIG. 12 depicts an example of a barrier wall and protrusion with interlocking or intermeshing surface profiles in the context of an OMM. The implementation of FIG. 12 is similar to that depicted in the example of FIG. 11. In this example, the protrusion 136 takes the form of a triangular cross-section, prismatic protrusion 136 that extends away from the window 104. The protrusion 136 has, in this example, a subset of two protrusion surfaces 142 that face towards a subset of barrier wall surfaces 140. In this example, the barrier wall 130, which is part of the OMM 122, also includes other barrier wall surfaces that are not in the subset of barrier wall surfaces 140, such as the left and right vertical side walls of the barrier wall 130.

As shown, there is a tolerance gap between the window 104 and the OMM 122. It is to be understood that the tolerance gap may, depending on the particular tolerance stack for any given biometric monitoring device, vary. In fact, in some instances, the tolerance gap may be reduced to zero, resulting in contact between the window and/or protrusion and the OMM 122 and/or the barrier wall 130.

As is evident, the subset of protrusion surfaces 142 may include at least one protrusion surface 142 that extends to a point further from the window 104 than a barrier wall surface 140 in the subset of barrier wall surfaces 140. This characteristic is to be understood as being inherent when two surface profiles "intermesh" or "interlock,", as the terms are used herein, with each other. In this example, the subset of the barrier wall surfaces 140 and the subset of the protrusion surfaces 142 have complementary profiles, i.e., the subset of protrusion surfaces 142 form a V-shaped ridge and the subset of barrier wall surfaces 140 form a V-shaped groove with the same included angle as is formed by the protrusion surfaces 142 in the subset of protrusion surfaces 142, that allow the two subsets of surfaces to come into intimate contact with one another if the tolerance gap is reduced to zero. At the same time, if the tolerance gap were to instead increase slightly or include a lateral offset in addition to or in place of a vertical offset, the intermeshing between the subset of the barrier wall surfaces 140 and the subset of the protrusion surfaces 142 would still prevent light following, for example, an optical path similar to the optical path 138 from the photo-emitter element 109, from passing between the protrusion 136 and the barrier wall 130 without first striking at least one protrusion surface 142 in the subset of the protrusion wall surfaces 142 and/or at least one barrier wall surface 140 in the subset of the barrier wall surfaces 140 before the light reaches the photodetector element 111. It is to be understood that it is not necessary that the subset of barrier wall surfaces 140 and subset of the protrusion surfaces 142 have complementary profiles in order to be viewed as intermeshing or interlocking, although some implementations with interlocking or intermeshing surface profiles may exhibit such a complementary relationship. For example, in some implementations of a V-shaped groove and a triangular protrusion feature that intermeshes with the V-shaped groove, the V-shaped groove and the triangular protrusion may have different included angles, e.g., the angles may be within ±10° of one another.

Figure 13:
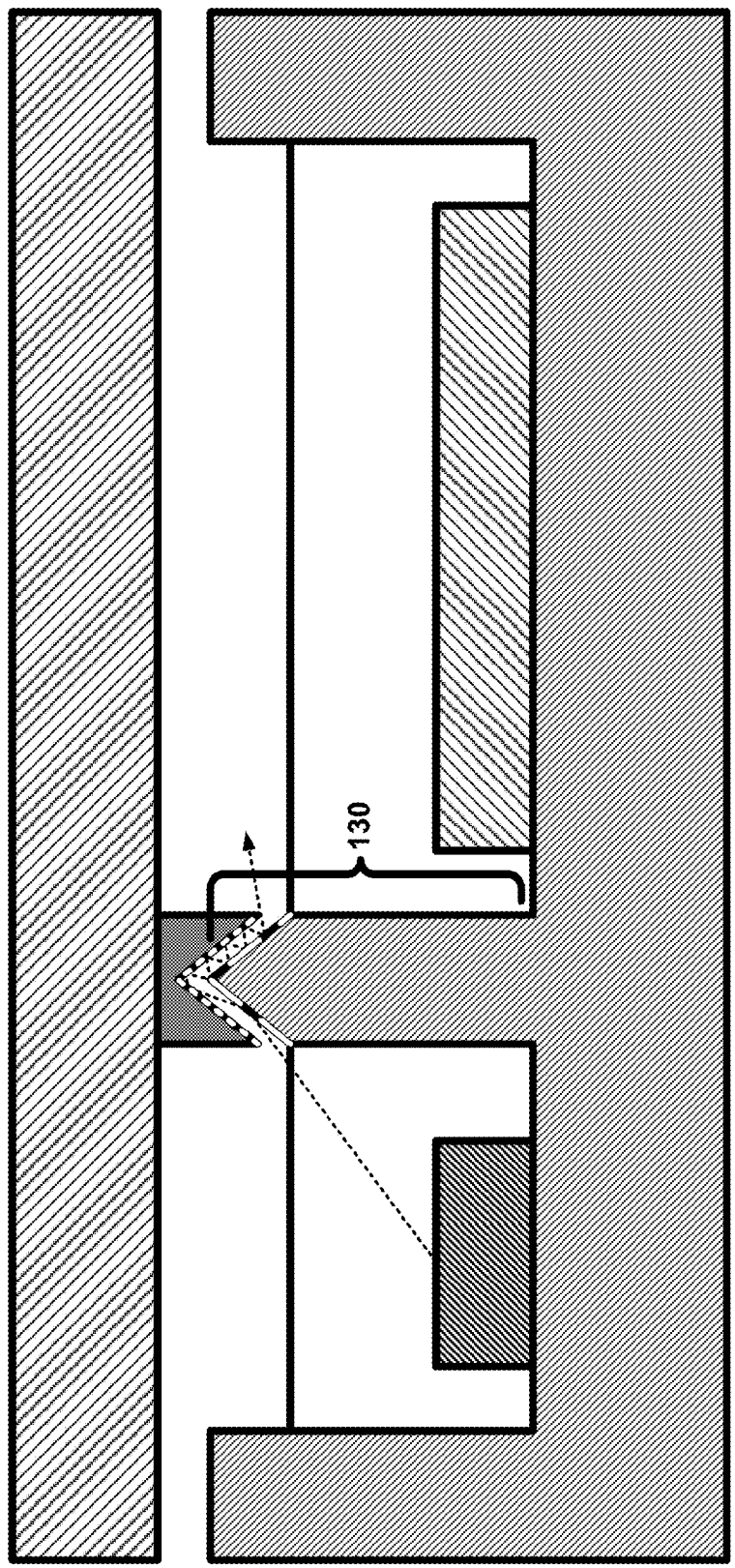
FIG. 13 depicts another example of a barrier wall and protrusion with interlocking or intermeshing surface profiles in the context of an OMM.

FIG. 13 depicts another example of a barrier wall and protrusion with interlocking or intermeshing surface profiles in the context of an OMM. In this example, the protrusion has protrusion surfaces that form left and right side walls, as well as a subset of protrusion surfaces 142 that form a V-shaped groove. In turn, the barrier wall 130 in this example has, in addition to barrier wall surfaces that form the left and right sides of the barrier wall, a subset of barrier wall surfaces 140 that face towards the subset of protrusion surfaces 142. In some respects, this is the inverse of the geometry shown in FIG. 12, and the observations made with respect to the implementation of FIG. 12 are equally applicable in this implementation.

Figure 14:
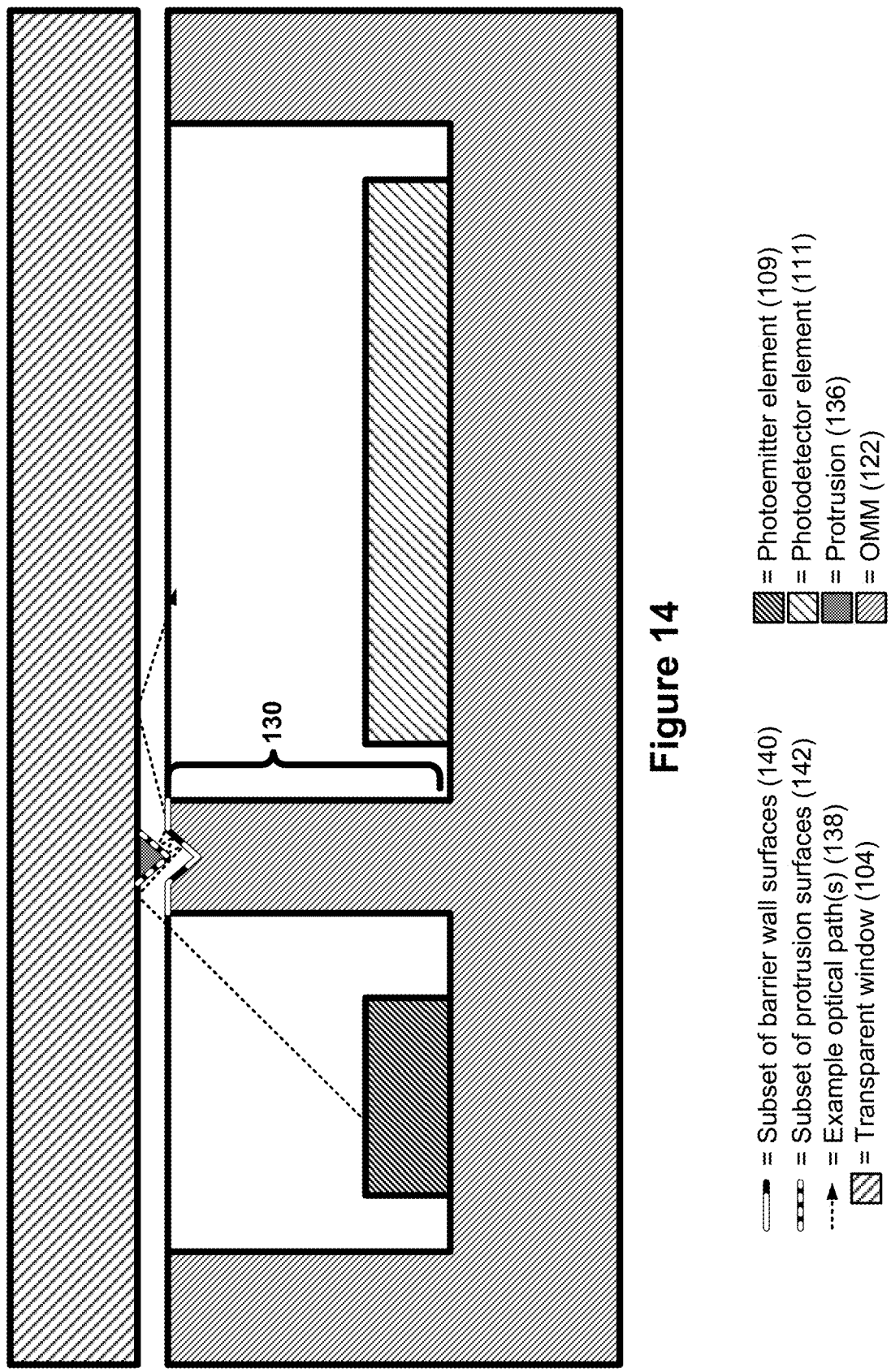
FIG. 14 depicts another example of a barrier wall and protrusion with interlocking or intermeshing surface profiles in the context of an OMM.

FIG. 14 depicts another example of a barrier wall and protrusion with interlocking or intermeshing surface profiles in the context of an OMM. In FIG. 14, the barrier wall 130 includes a subset of barrier wall surfaces 140 that form a V-shaped groove with short landings on either side that are parallel to and coincident with the top surface of the OMM 122. In many respects, this implementations is similar to that of FIG. 12. However, the short landings may offer a more robust transition between the V-shaped groove and the barrier wall surfaces that form the left and right side walls of the barrier wall as compared with the "knife-edge" transition shown in FIG. 12.

Figure 15:
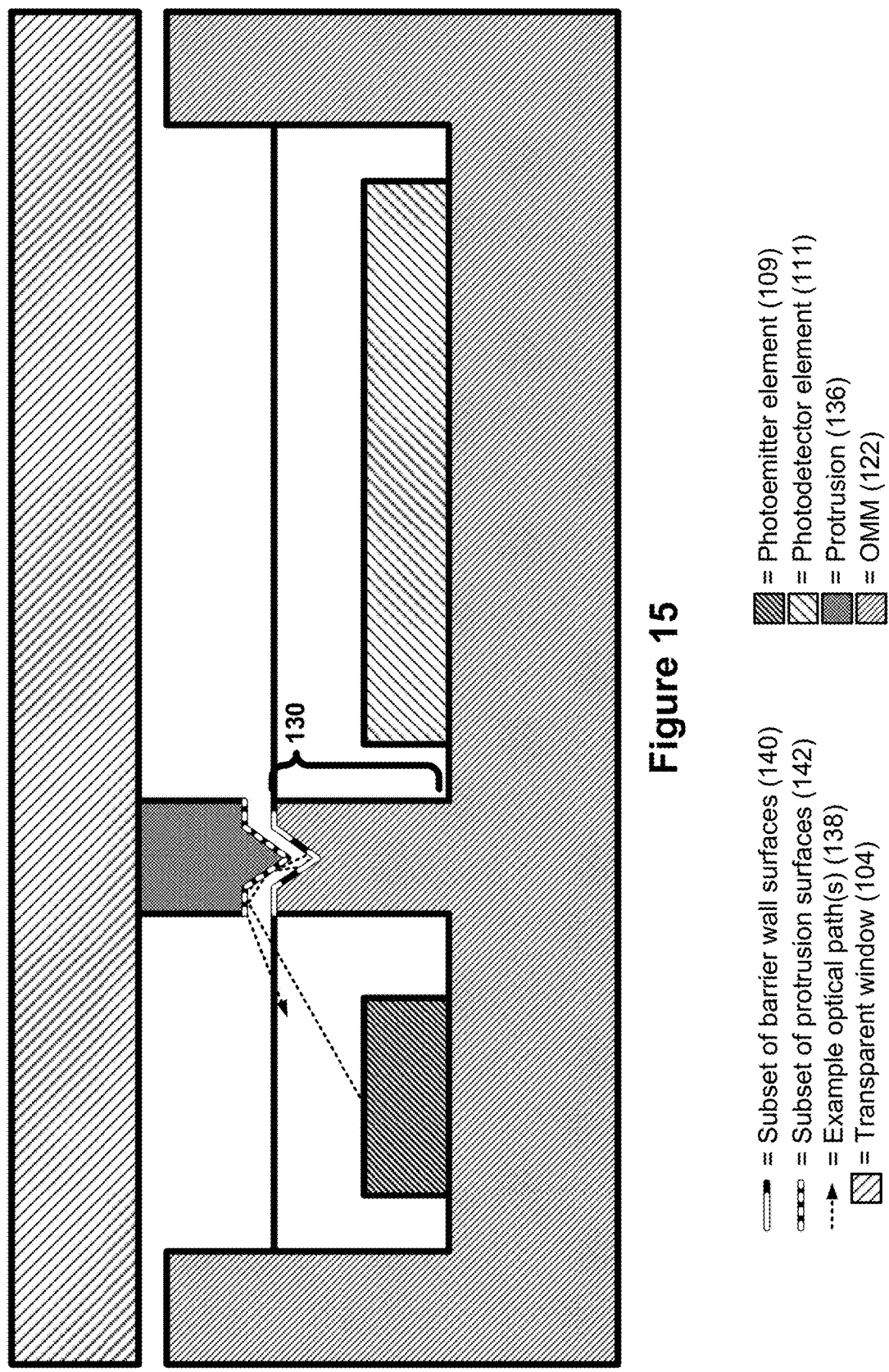
FIG. 15 depicts another example of a barrier wall and protrusion with interlocking or intermeshing surface profiles in the context of an OMM.

FIG. 15 depicts another example of a barrier wall and protrusion with interlocking or intermeshing surface profiles in the context of an OMM. The implementation of FIG. 15 is similar to that depicted in FIG. 14, except that the barrier wall 130 is shorter and the protrusion 136 extends away from the window 104 to a greater extent and the subset of protrusion surfaces 142 define a triangular cross-section, prismatic profile that is flanked by landings on both sides that extend away from the triangular prismatic profile in a manner similar to how the landings in the subset of barrier wall surfaces extend away from the V-shaped groove.

Figure 16:
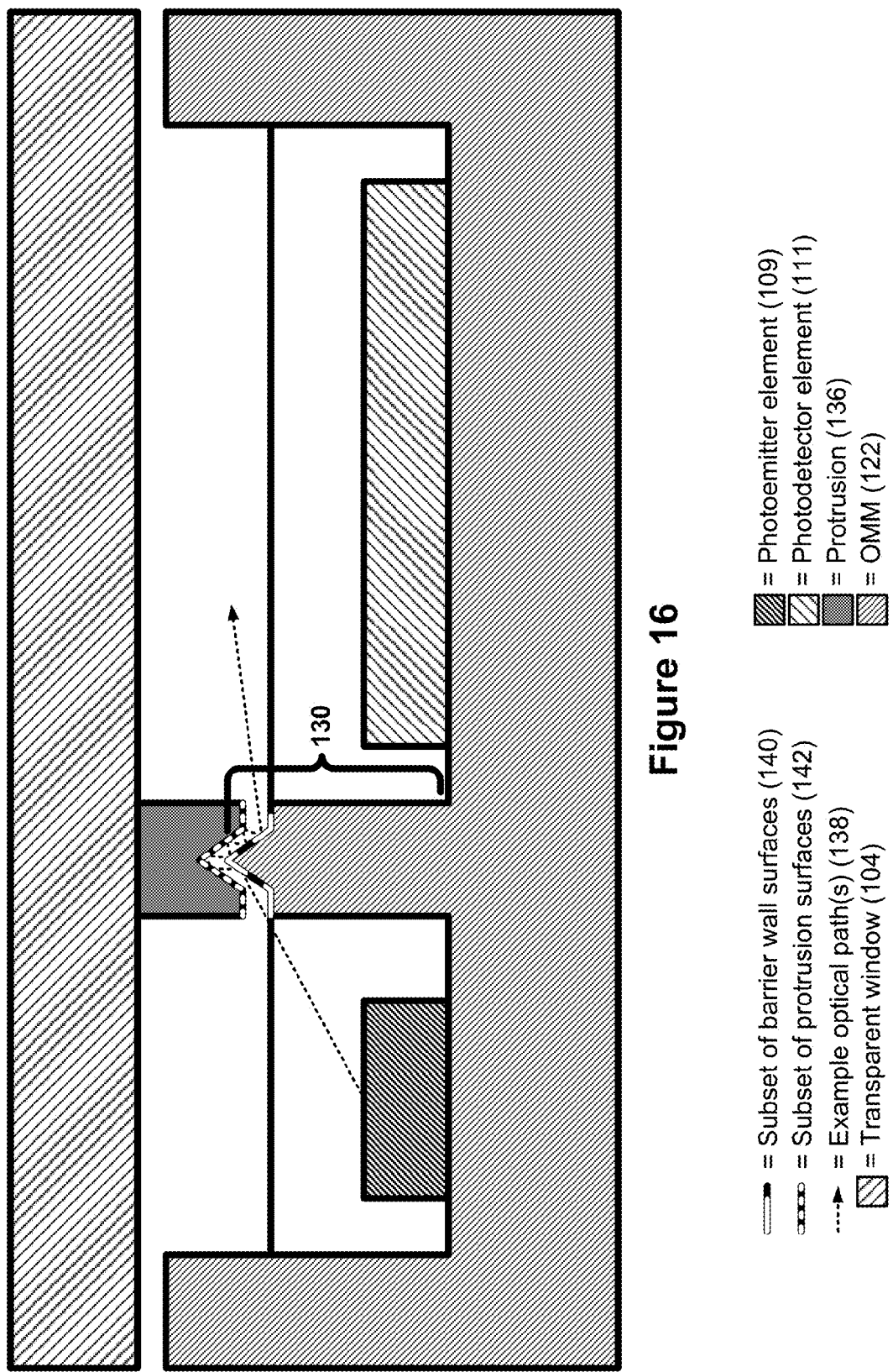
FIG. 16 depicts another example of a barrier wall and protrusion with interlocking or intermeshing surface profiles in the context of an OMM.

FIG. 16 depicts another example of a barrier wall and protrusion with interlocking or intermeshing surface profiles in the context of an OMM. The implementation in FIG. 16 is similar to that of FIG. 15, except that the V-shaped groove is located in the protrusion, and the triangular prismatic cross-section surface profile is located in the barrier wall.

Figure 17:
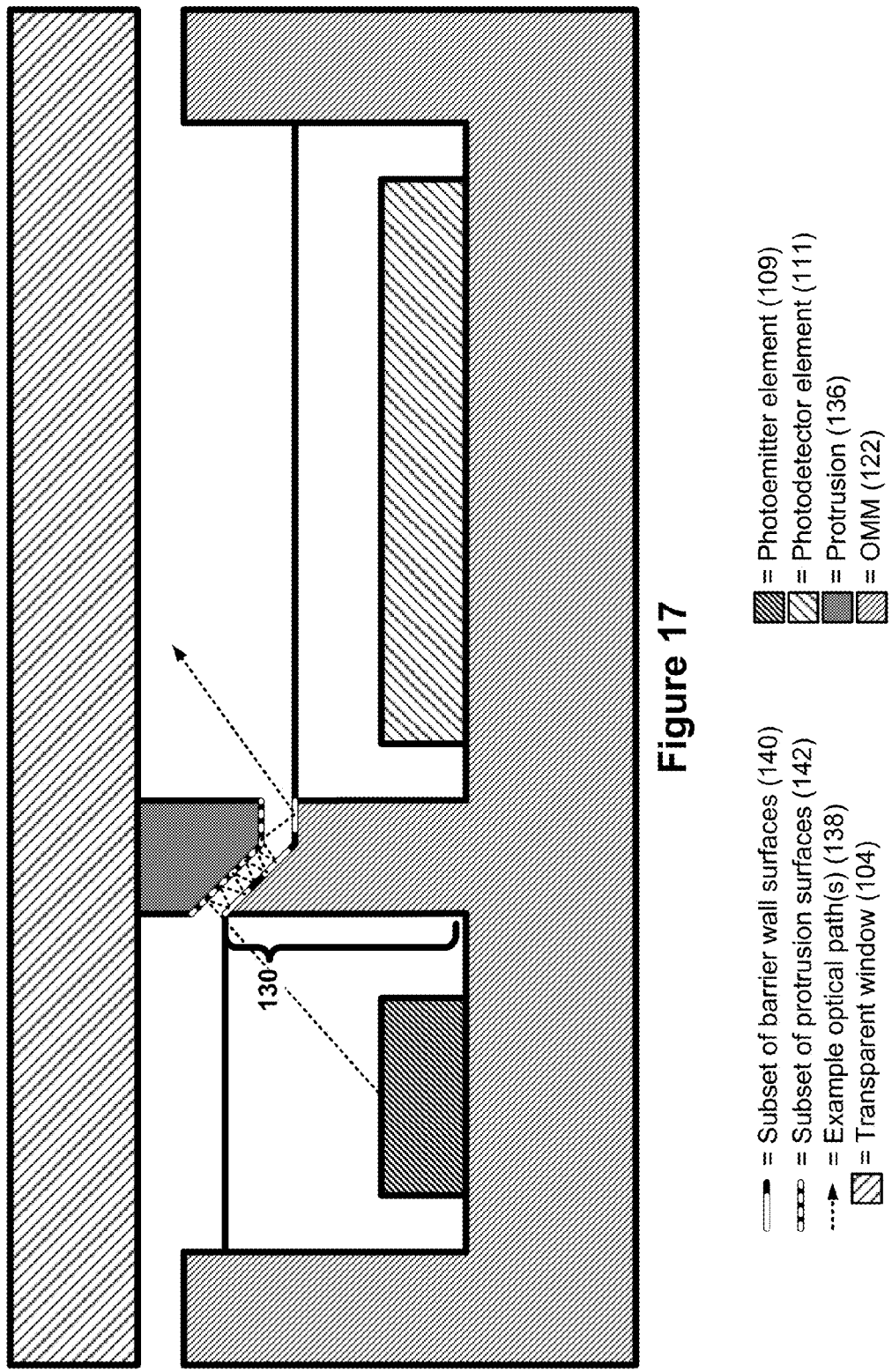
FIG. 17 depicts another example of a barrier wall and protrusion with interlocking or intermeshing surface profiles in the context of an OMM.

FIG. 17 depicts another example of a barrier wall and protrusion with interlocking or intermeshing surface profiles in the context of an OMM. Whereas the previous example implementations have featured symmetric barrier walls 130 and protrusions 136, some implementations may feature asymmetric barrier walls 130 and/or protrusions 136. The implementation of FIG. 17 is an example of such an asymmetric design. As can be seen, the subset of barrier wall surfaces 140 and the subset of protrusion surfaces 142 each include a "horizontal" surface and an "oblique" surface, i.e., there are at least two surfaces in the subsets of barrier wall surfaces and protrusion surfaces that are at an angle with respect to one another (an angle less than 180° and greater than 0°). In the depicted example, the angle is approximately 45° or 135° (depending on the direction of measurement), although greater or smaller oblique angles may be used as well.

Figure 18:
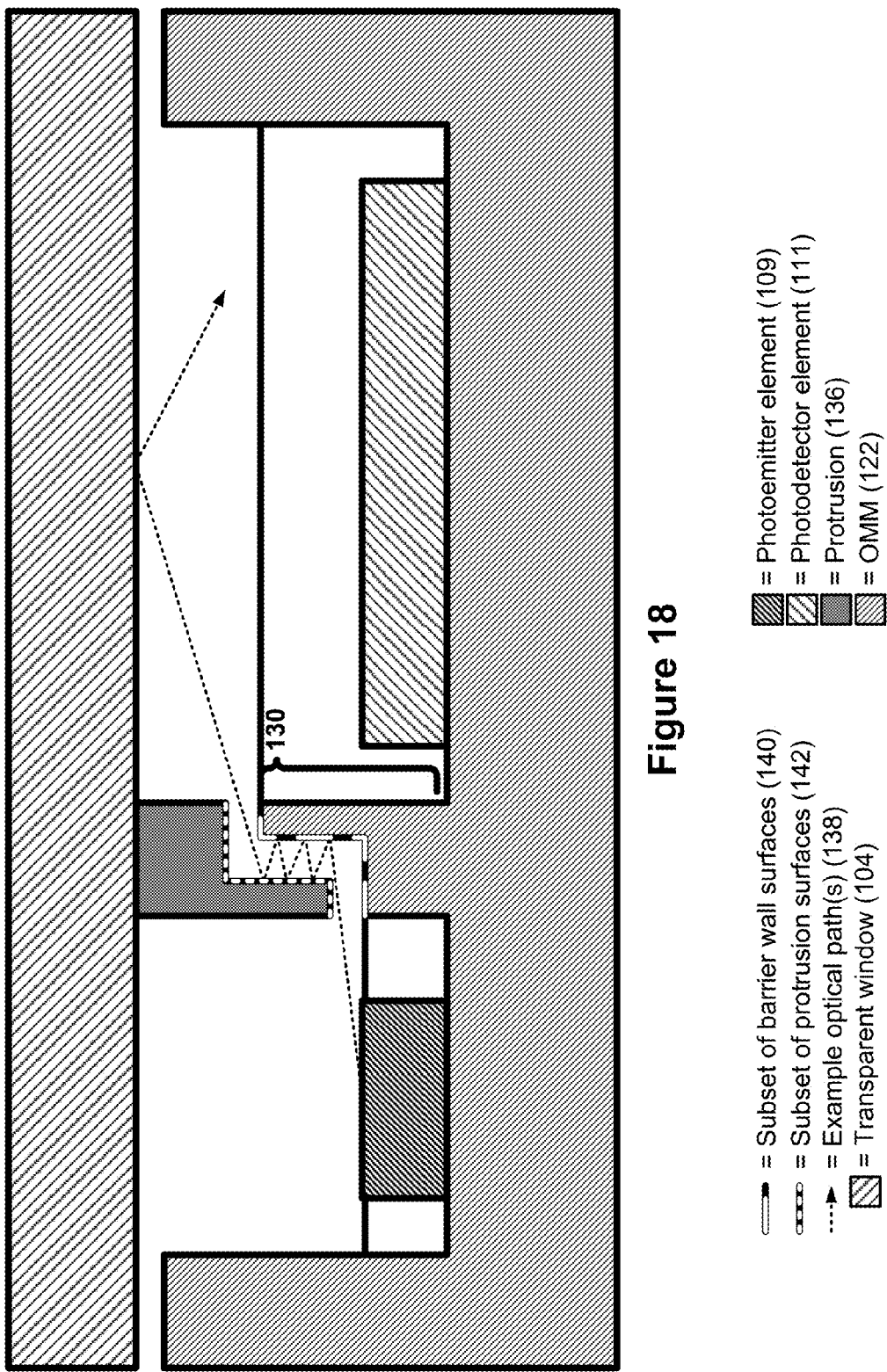
FIG. 18 depicts another example of a barrier wall and protrusion with interlocking or intermeshing surface profiles in the context of an OMM.

FIG. 18 depicts another example of a barrier wall and protrusion with interlocking or intermeshing surface profiles in the context of an OMM. In the previous examples, the subset of protrusion surfaces 142 and the subset of barrier wall surfaces 140 have exhibited profiles having at least one oblique angle (relative to the horizontal axis of each Figure). However, some implementations, such as the implementation of FIG. 18, may have a subset of protrusion surfaces 142 and a subset of barrier wall surfaces 140 that are, as depicted in FIG. 18, orthogonal to one another, e.g., forming stair-step patterns or other "step-function"-like profiles.

Figure 19:
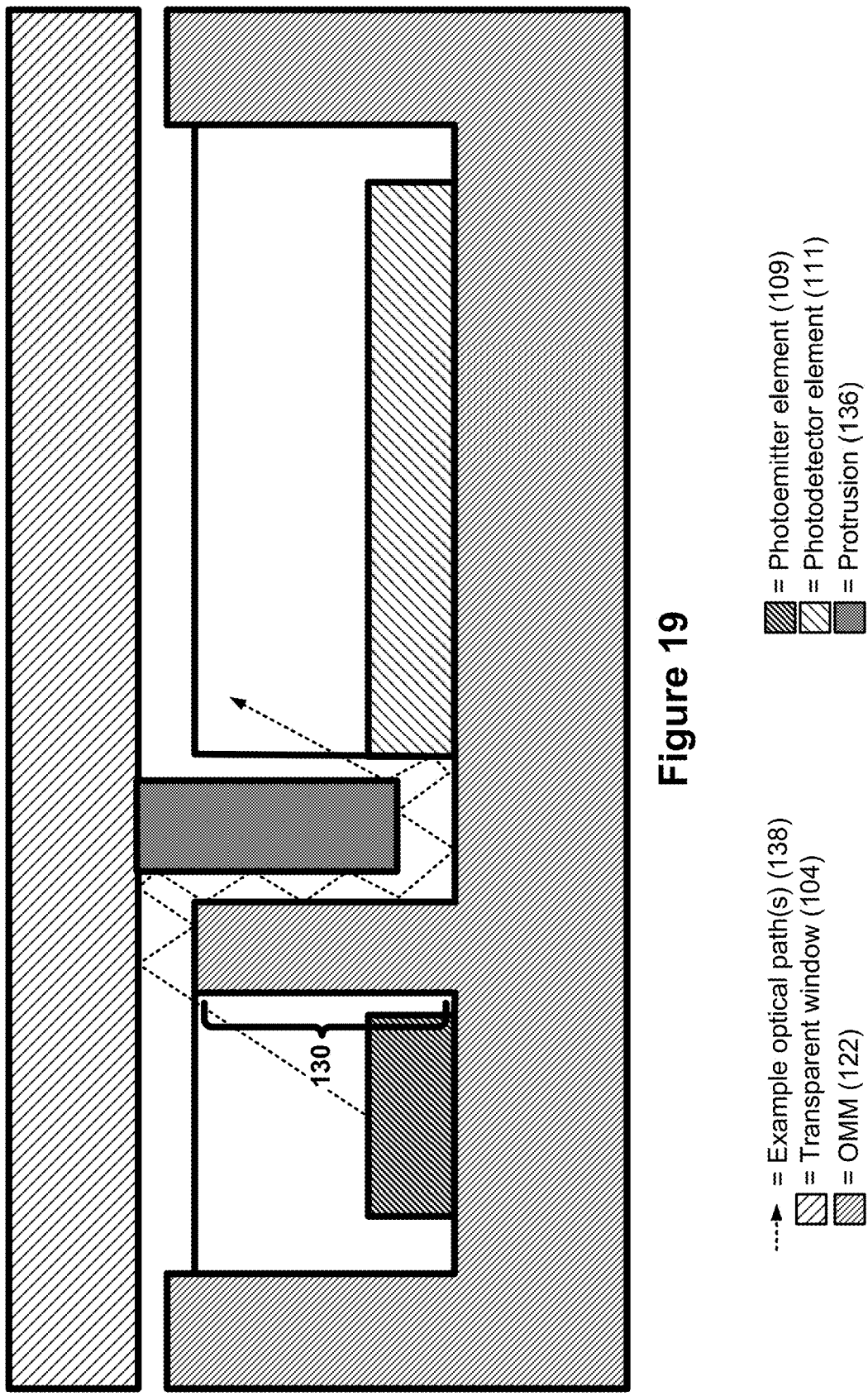
FIG. 19 depicts an example of a barrier wall and protrusion that interlock or intermesh with one another in the context of an OMM.

In all of the implementations of FIGS. 12 through 18, the barrier walls 130 and the protrusions 136 overlap one another, at least partially, when viewed along an axis perpendicular to the window 104 at the location where the protrusion 136 is located. However, in some other implementations, the barrier wall 130 and the protrusion 136 may not overlap when viewed along such an axis, but may instead intermesh as a whole. FIG. 19 depicts an example of a barrier wall and protrusion that interlock or intermesh with one another in the context of an OMM. As can be seen in this example implementation, the barrier wall 130 and the protrusion 136 may both, in effect, be walls and may be offset laterally from one another so as to form a convoluted optical path for any light that happens to pass into the gap, if any, between the barrier wall 130 and the protrusion 136.

The barrier wall and protrusion features described above may, along with other, similar barrier wall and protrusion features with interlocking or intermeshing surface profiles, offer a two-piece light leakage barrier that is particularly well-suited for preventing light leakage in optical measurement modules or other optical sensor modules having very small feature sizes, e.g., on the other of 4-8 mm in maximum dimension, with gaps between the photo-emitter element centers and the photodetector element edges that are on the order of 1.5 mm to 3 mm, e.g., less than or equal to 2.6 mm, and a barrier wall thickness on the order of 1 mm to 2 mm or less. Due to their two-piece construction, such light leakage barriers may accommodate tolerance gap variability that might result in light leakage between the photo-emitters and photodetector of an OMM or other optical sensor having a similar arrangement of photo-emitters and photo-detector(s). This ability of such features to accommodate variability in the tolerance gap is discussed in more detail with respect to two different implementations depicted in the following Figures.

Figure 20:
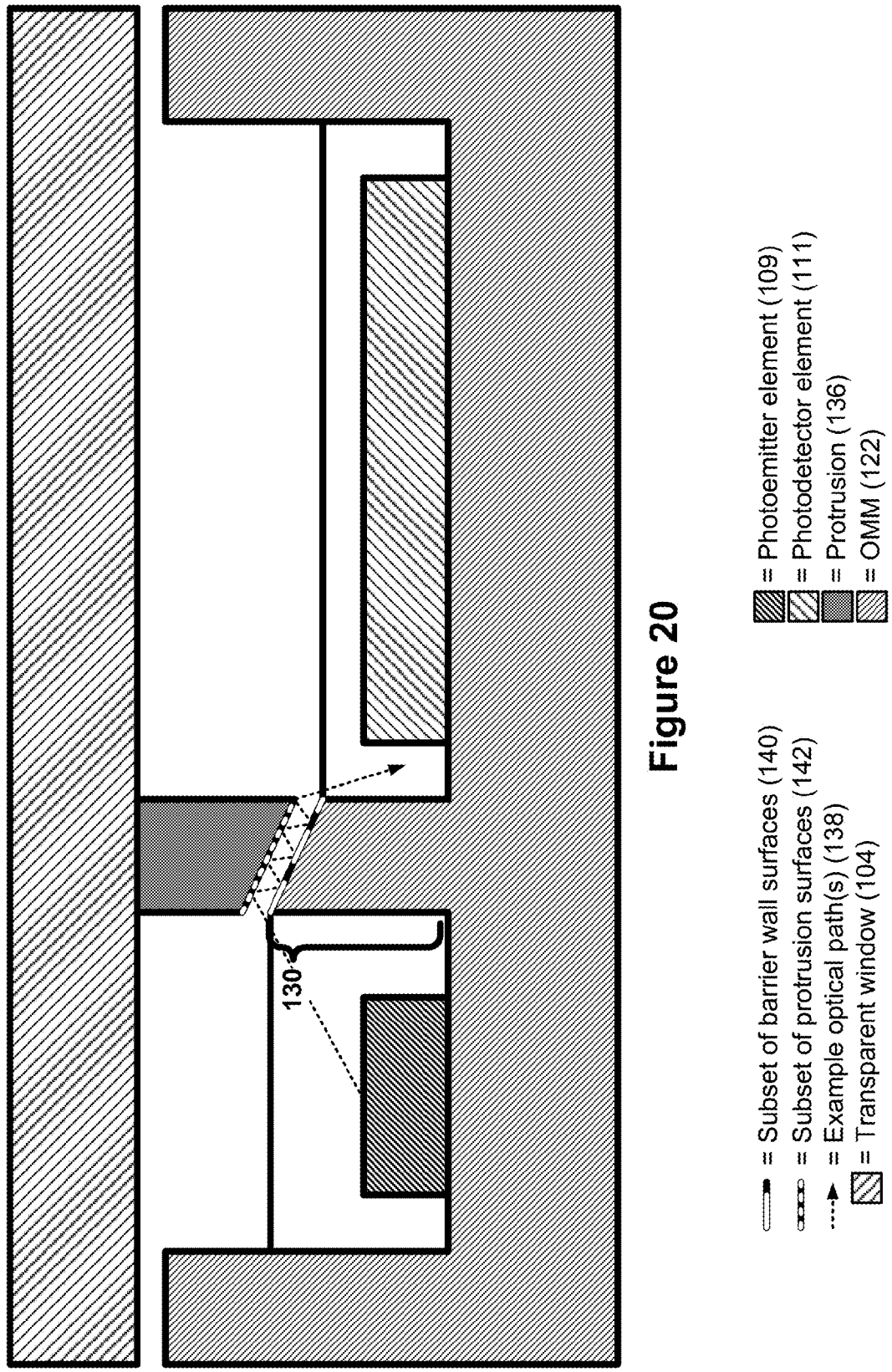
FIG. 20 depicts another example of a barrier wall and protrusion with interlocking or intermeshing surface profiles in the context of an OMM.
Figure 21:
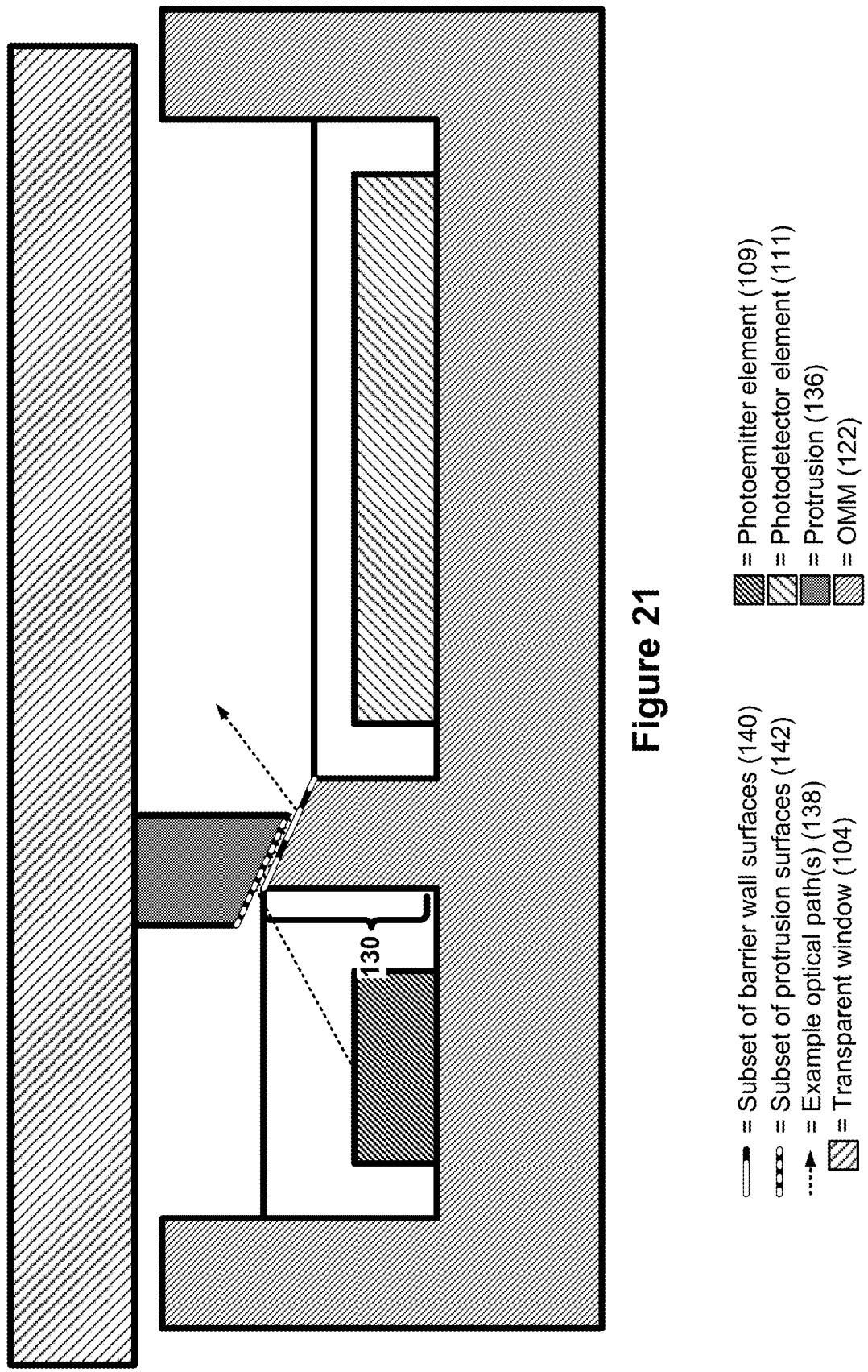
FIG. 21 depicts the example barrier wall and protrusion of FIG. 20 but with a lateral tolerance offset between the window and the OMM.
Figure 22:
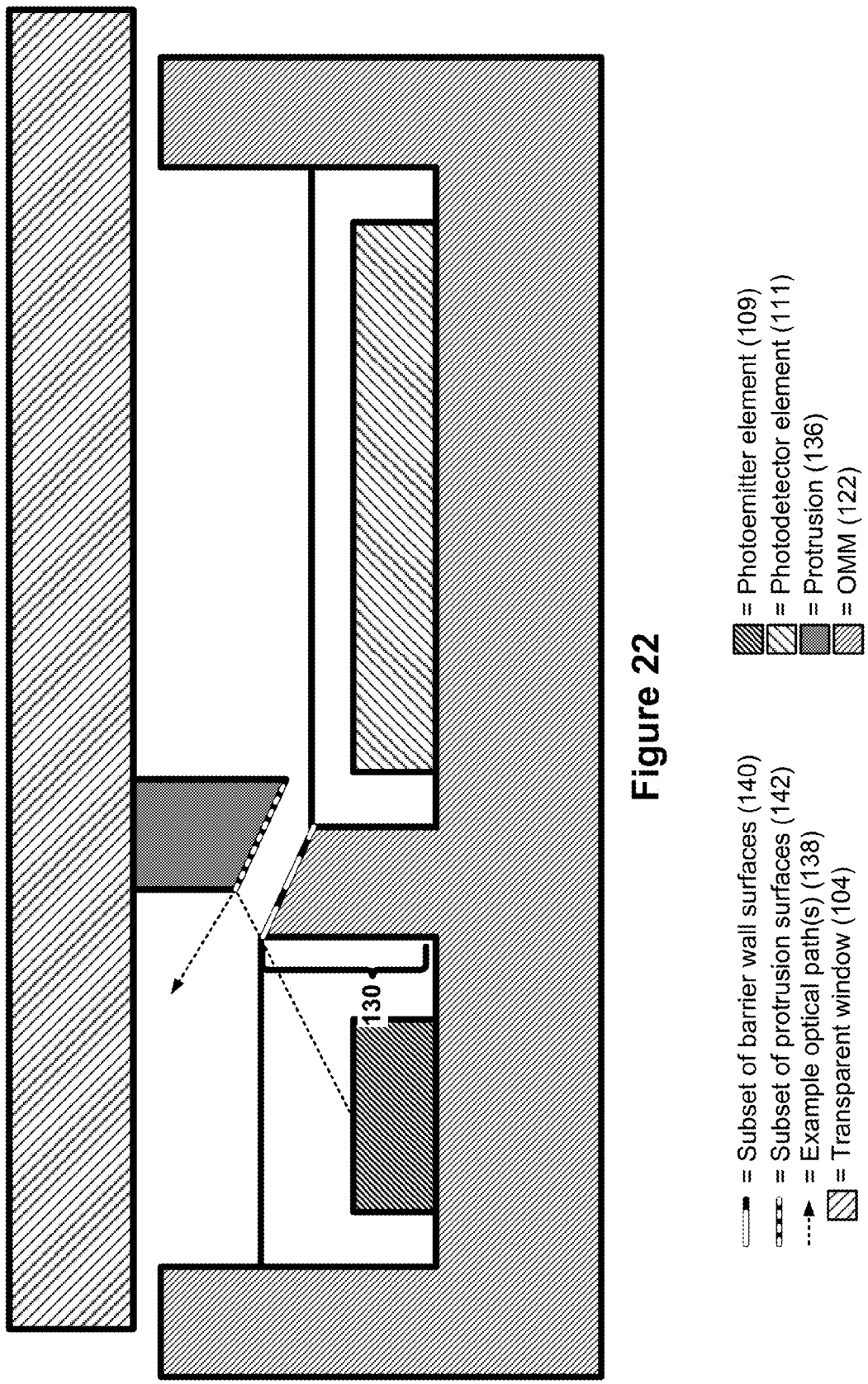
FIG. 22 depicts the example barrier wall and protrusion of FIG. 20 but with a different lateral tolerance offset between the window and the OMM.

FIG. 20 depicts another example of a barrier wall and protrusion with interlocking or intermeshing surface profiles in the context of an OMM. FIG. 21 depicts the example barrier wall and protrusion of FIG. 20 but with a lateral tolerance offset between the window and the OMM. FIG. 22 depicts the example barrier wall and protrusion of FIG. 20 but with a different lateral tolerance offset between the window and the OMM.

In FIGS. 20 through 22, the protrusion 136 has a subset of a single protrusion surface 142 that faces a corresponding subset of a single barrier wall surface 140 of the barrier wall 130. In this example, the barrier wall surface 140 and the protrusion surface 142 in the subsets are both sloped such that the edges of these surfaces closest to the photo-emitter element 109 is closer to the window 104 than the edges of these surfaces closest to the photodetector element 111. This arrangement guarantees that light traveling directly towards the interface between the protrusion 136 and the barrier wall 130 from the photo-emitter element 109 is forced to impinge on at least the protrusion surface 142 and, in all likelihood, multiple times on both the protrusion surface 142 and the barrier wall surface 140.

As can be seen, due to the geometry of the barrier wall 130 and the protrusion 136, the window 104 may be able to suffer some lateral misalignment, e.g., such as 0.1 mm or 0.2 mm of lateral misalignment, relative to the OMM 122 without allowing for optical paths, such as optical paths 138, from the photo-emitter element 109 to reach the photodetector element 111 without first impinging the barrier wall surface 140 and/or the protrusion surface 142.

Figure 23:
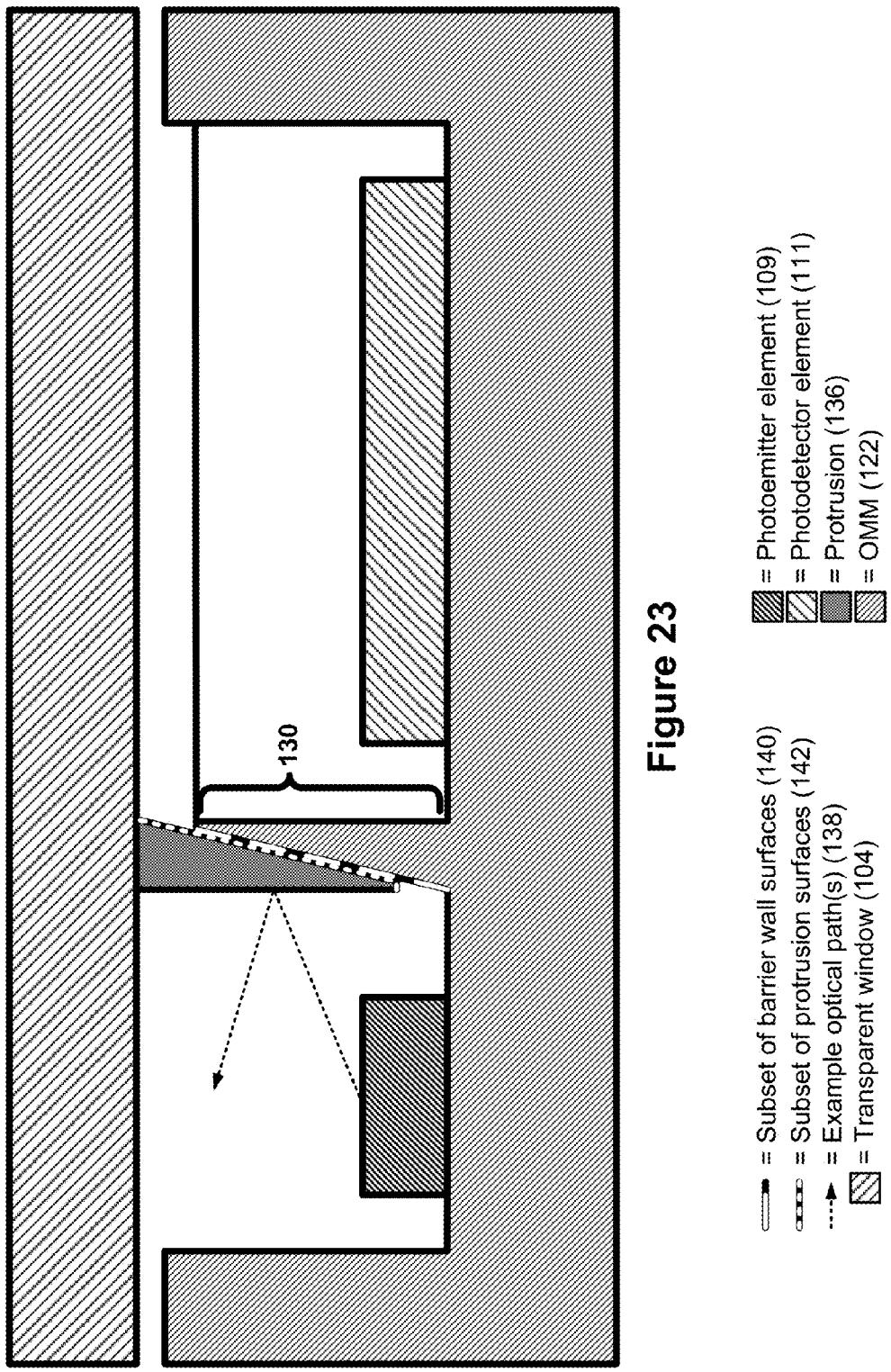
FIG. 23 depicts another example of a barrier wall and protrusion with interlocking or intermeshing surface profiles in the context of an OMM.
Figure 24:
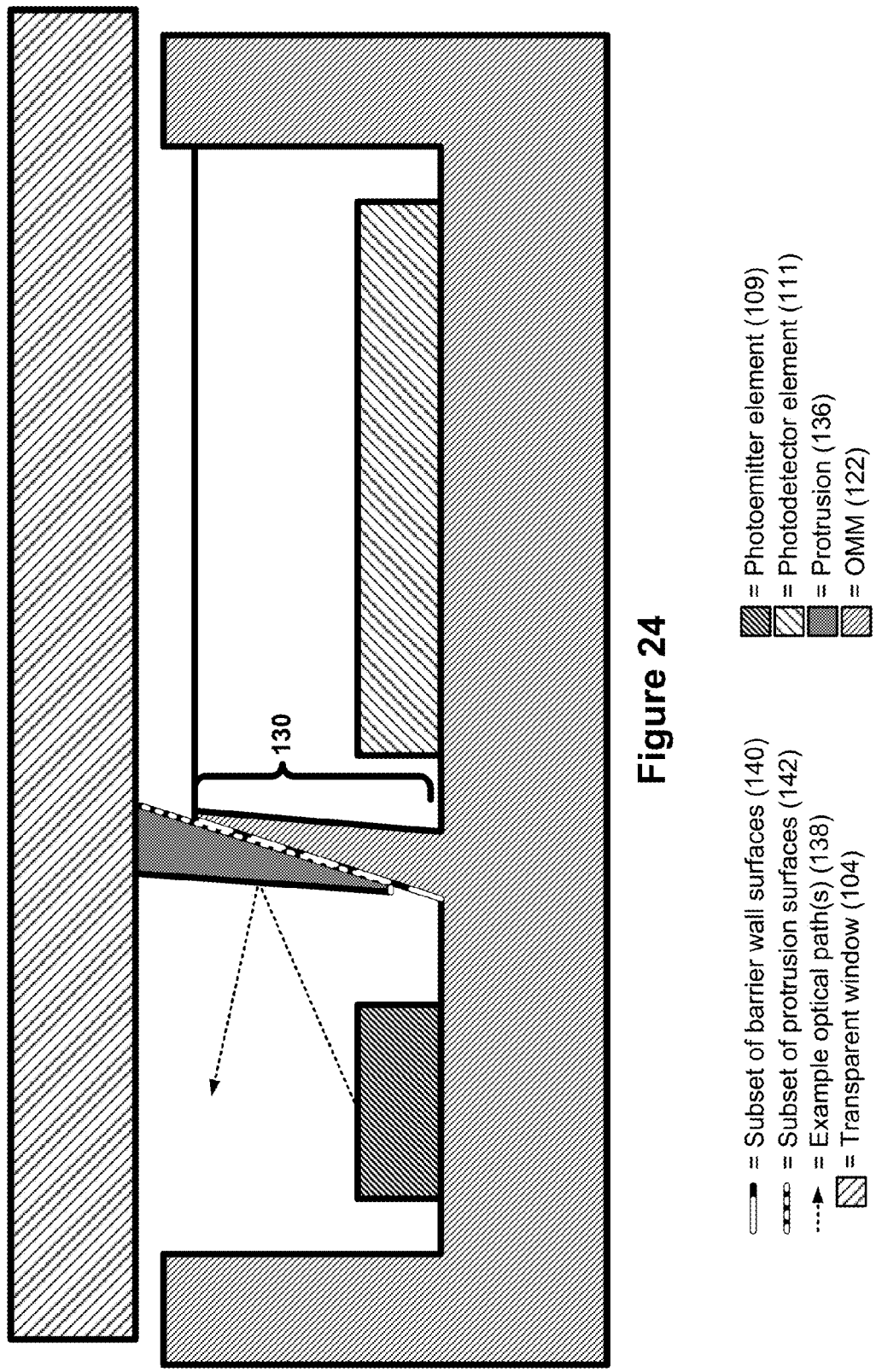
FIG. 24 depicts the example barrier wall and protrusion of FIG. 23 but with a lateral tolerance offset between the window and the OMM.
Figure 25:
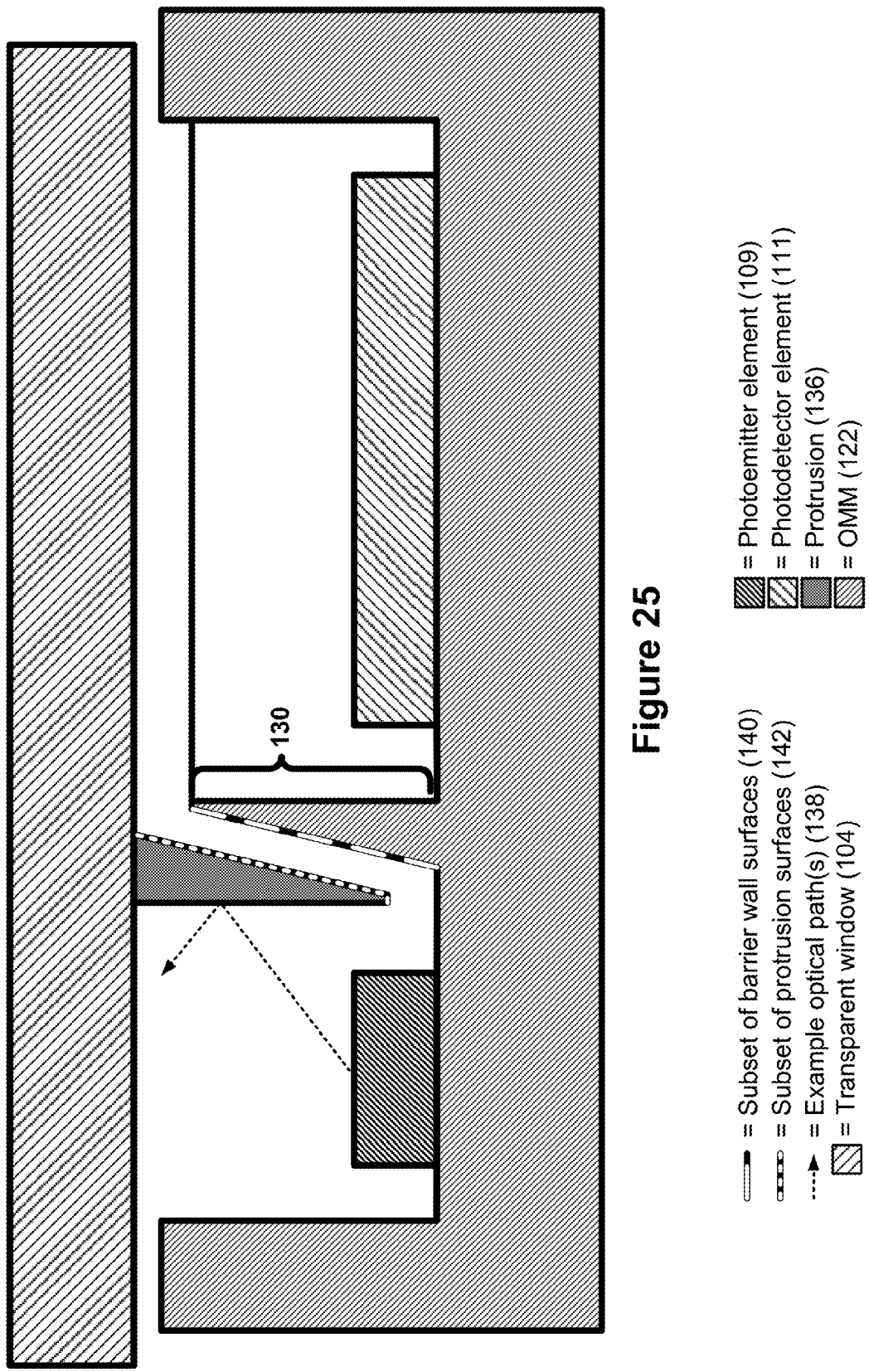
FIG. 25 depicts the example barrier wall and protrusion of FIG. 23 but with a different lateral tolerance offset between the window and the OMM.

FIG. 23 depicts another example of a barrier wall and protrusion with interlocking or intermeshing surface profiles in the context of an OMM. FIG. 24 depicts the example barrier wall and protrusion of FIG. 23 but with a lateral tolerance offset between the window and the OMM. FIG. 25 depicts the example barrier wall and protrusion of FIG. 23 but with a different lateral tolerance offset between the window and the OMM.

In FIGS. 23 through 25, the protrusion 136 and the barrier wall 130 both have cross-sectional shapes that are long, thin triangular prisms. Such a barrier wall 130 and protrusion 136 may be able to accommodate even more lateral tolerance offset between the window 104 and the OMM 122 than the previous implementation since the barrier wall 130 and the protrusion 136 may, due to their long, thin cross-sectional profiles, flex when forced into contact with one another. Such flexure may allow the window 104 to experience even greater lateral translation with respect to the OMM 122, and it may also allow for a more light-tight interface between the protrusion 136 and the barrier wall 130 since the beam restoring force generated by such flexure will press at least a portion of the subset of barrier wall surfaces 140 into intimate contact with at least a portion of the subset of protrusion surfaces 142.

In addition to the above examples featuring protrusions and barrier walls with interlocking or intermeshing surface profiles (or barrier walls and protrusions that interlock or intermesh with one another as a whole), the present inventors also conceived of some alternative light-leakage barrier designs that may also provide good light leakage protection but that either do not require a barrier wall or do not require a protrusion. In these alternate implementations, a negative space of some sort may be provided on either the substrate or PCB to which the photo-emitter(s) and photodetector(s) are mounted or the window 104, and a barrier wall or a protrusion may then interlock or intermesh with the negative feature. A negative feature, in this context, refers to a feature such as a slot, hole, groove, or recess.

Figure 26:
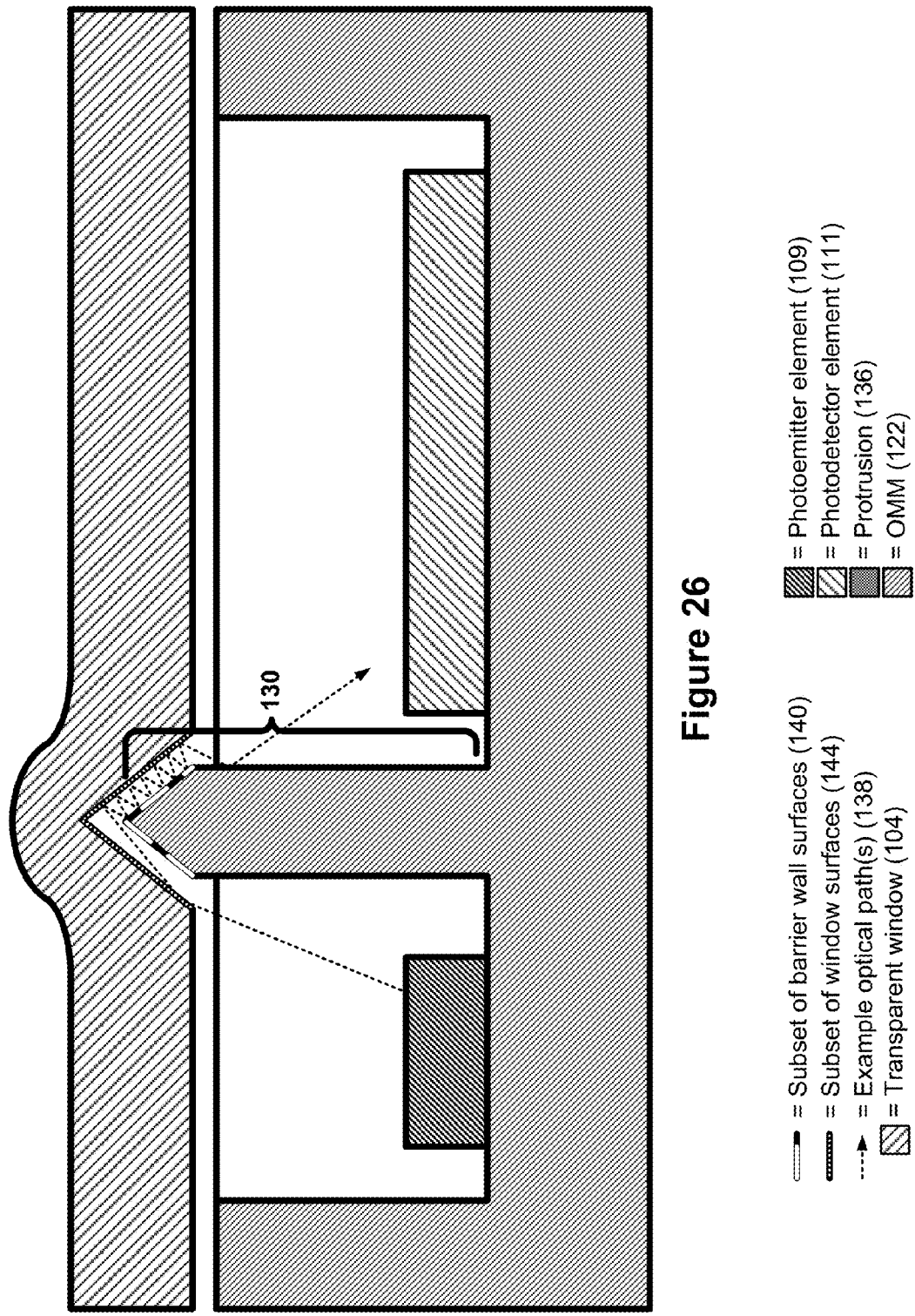
FIG. 26 depicts an example of a barrier wall that intermeshes or interlocks with a groove on a window placed over an OMM.

FIG. 26 depicts an example of a barrier wall that intermeshes or interlocks with a groove on a window placed over an OMM. In FIG. 26, the OMM 122 has a barrier wall 130 that protrudes above the top surface of the OMM 122. The window 104 in this example does not include a protrusion, but instead has a subset of window surfaces 144 that define a V-shaped groove in the interior surface of the window 104. In this example, the window 104 has a bulge or other convex area on the exterior surface of the window 104 in an area that corresponds with the V-shaped groove, which may provide additional material to reinforce the window in the area of the subset of window surface 144.

Figure 27:
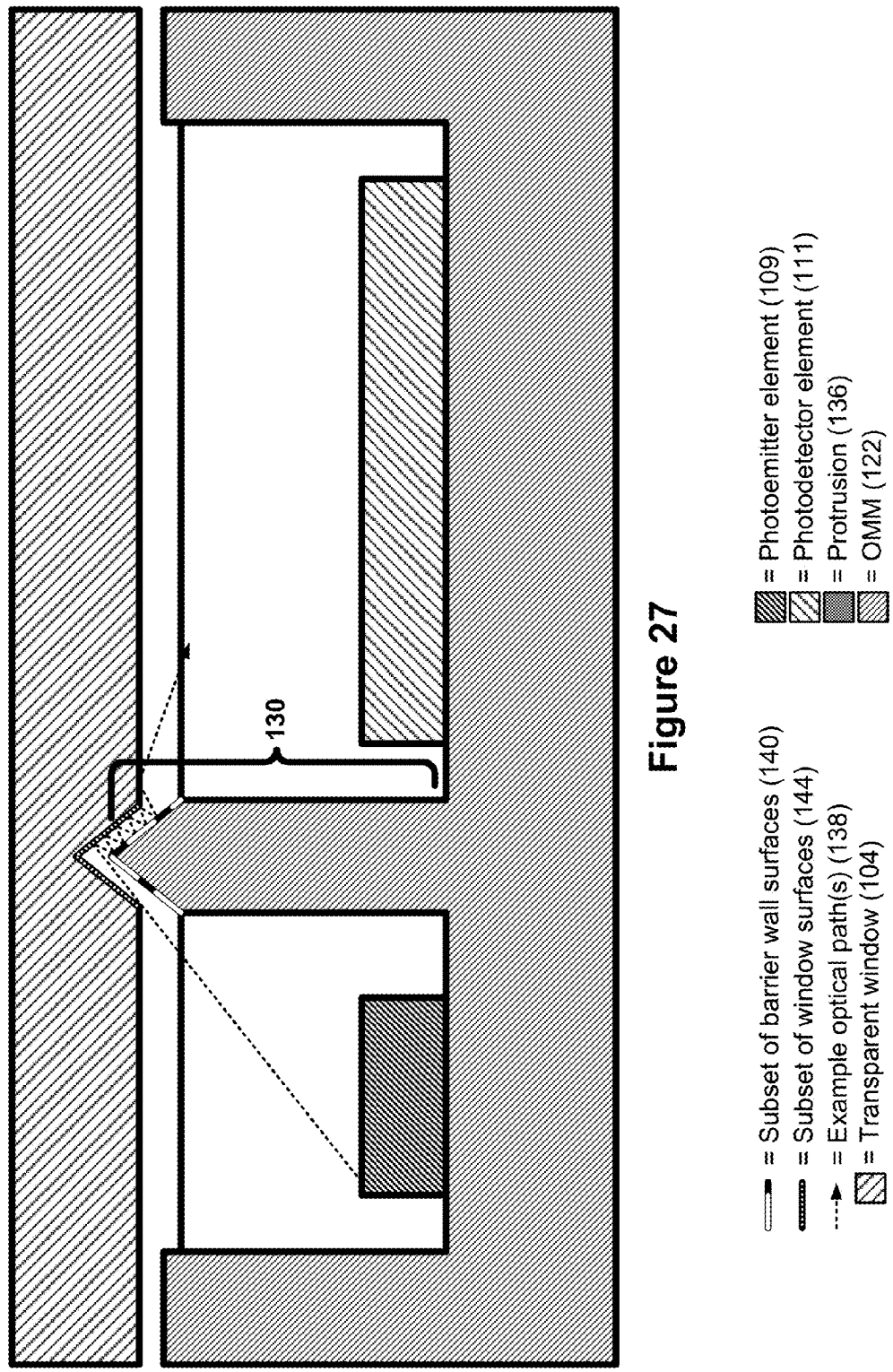
FIG. 27 depicts another example of a barrier wall that intermeshes or interlocks with a groove on a window placed over an OMM.

FIG. 27 depicts another example of a barrier wall that intermeshes or interlocks with a groove on a window placed over an OMM. This implementation is similar to the implementation of FIG. 26, except that the window 104 has an exterior surface that is unbroken by a bulge or convexity in the vicinity of the V-shaped groove.

As mentioned earlier, another implementation of which the present inventors conceived is one in which the substrate or PCB on which the photo-emitter elements 109 and the photodetector element 111 are mounted has a slot, recess, or other negative space feature that interlocks with or intermeshes with a protrusion located on the window 104.

Figure 28:
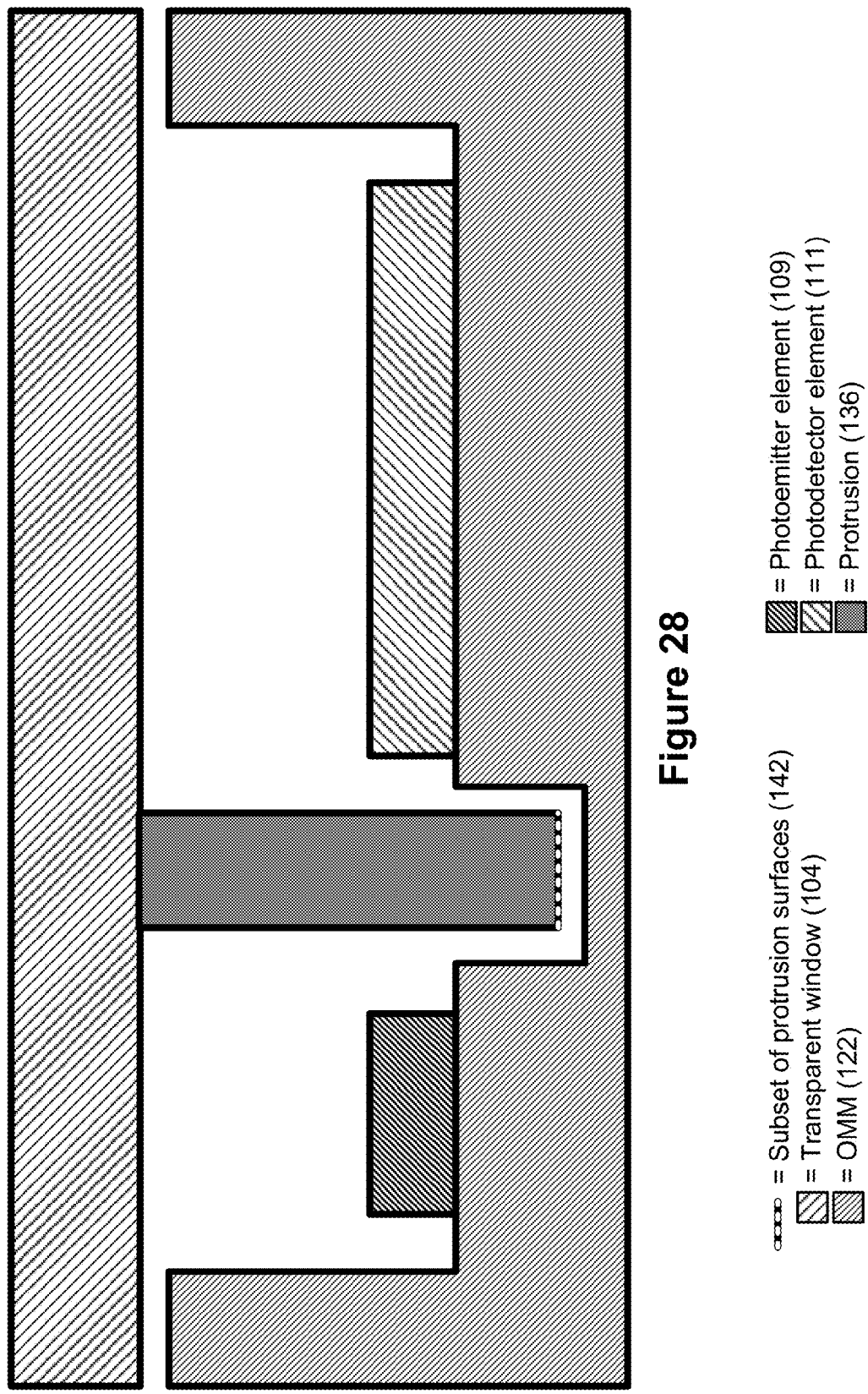
FIG. 28 depicts an implementation where the substrate of an OMM has a recess that may receive the end of a protrusion that extends from the window.

FIG. 28 depicts an implementation where the substrate of an OMM has a recess that may receive the end of a protrusion 136 that extends from the window 104. Such an arrangement may be very effective in terms of preventing light leakage between the photo-emitter elements 109 and the photodetector element 111, but the existence of such a trench or recess may interfere with conductive traces that are embedded within the substrate. Such a trench or recess may also make the OMM 122 slightly weaker, although these potential issues may be dealt with through proper engineering and layout.

Figure 29:
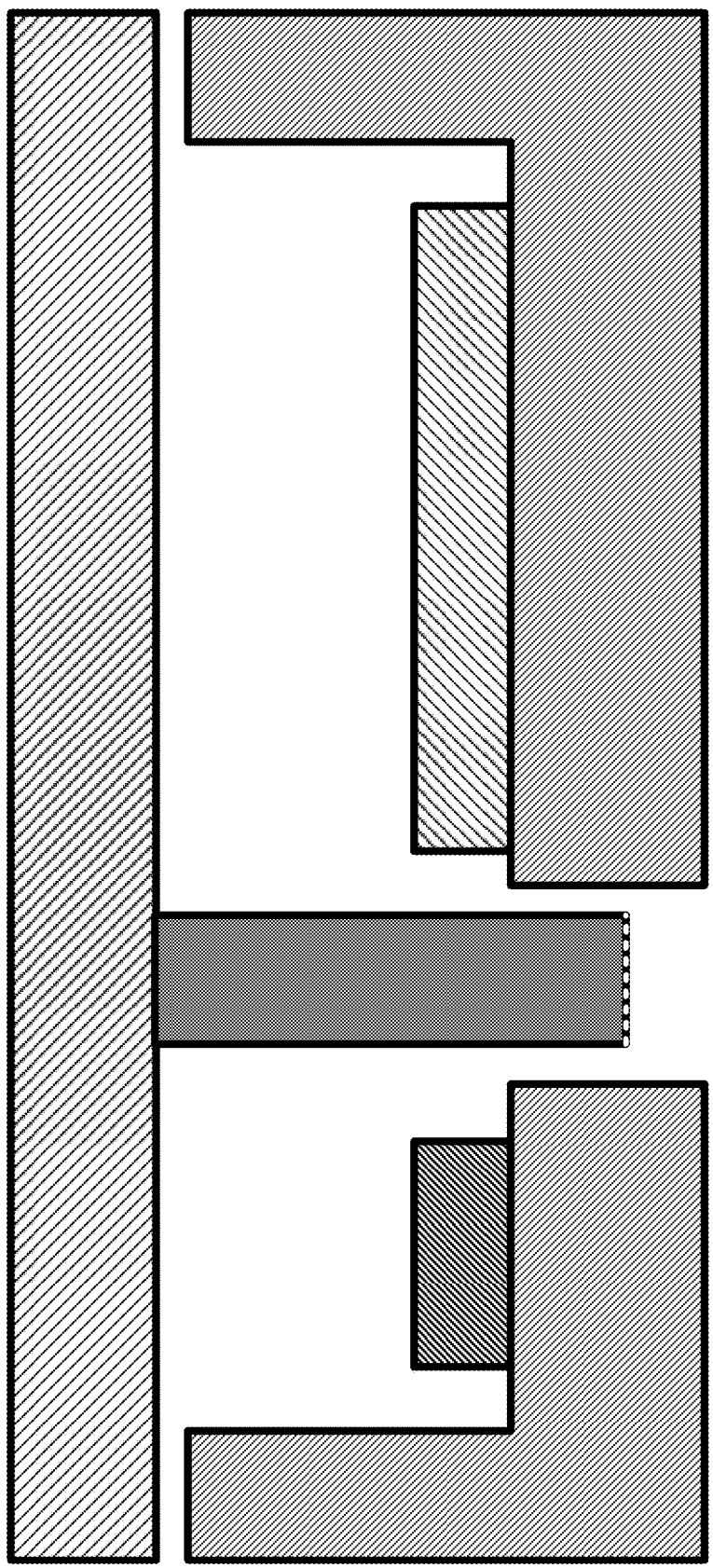
FIG. 29 depicts a further variant of the implementation in FIG. 28.

FIG. 29 depicts a further variant of the implementation in FIG. 28, although in this implementation, the recess extends through the PCB or the substrate entirely, which may provide even better protection against light leakage, as such an arrangement does not have any surface at the bottom of the recess or trench that can reflect light.

Figure 30:
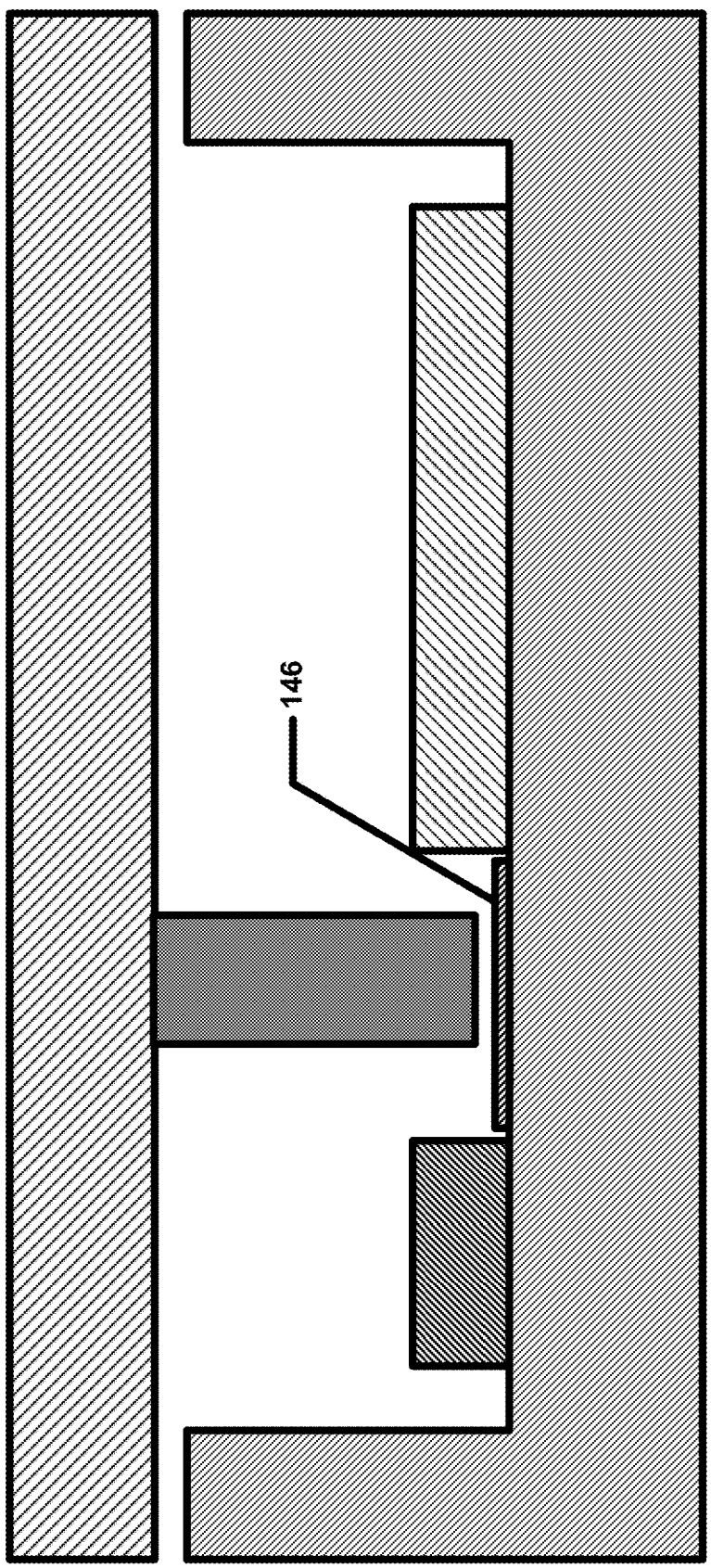
FIG. 30 depicts an implementation where a protrusion from a window extends towards a region of a PCB or substrate that is coated with an opaque material.

In addition to the various implementations discussed above, the present inventors also determined that another technique that may have efficacy in terms of preventing light leakage. FIG. 30 depicts an implementation where a protrusion from a window extends towards a region of a PCB or substrate that is coated with an opaque material, for example, such as film 146. Such a coating may, for example, be a metal or other light-opaque material that prevents light from the photo-emitter element from entering the substrate or the PCB on which the photo-emitter element and photodetector element are located. In many substrates or PCBs, light that enters the substrate or PCB may diffuse through the substrate or PCB and may thus bypass the light-blocking ability of the protrusion and potentially reach the photodetector element. The present inventors determined that if the surface of the substrate or PCB facing towards the protrusion were to have a thin layer of light-opaque material deposited thereon across the entire region between the photo-emitter element(s) and the protrusion or the side of the protrusion facing the photodetector element, then this would prevent such an occurrence from happening. In some cases, this region may already be partially occupied by solder contact pads, in which case additional metal plating may be deposited around the solder contact pads (leaving a small gap between the solder contact pads and the additional metal plating to prevent short-circuits) in order to fill the region with the opaque coating to the greatest extent possible. Such an implementation may be practiced as shown, or in conjunction with the other techniques and structures discussed herein.

Figure 31:
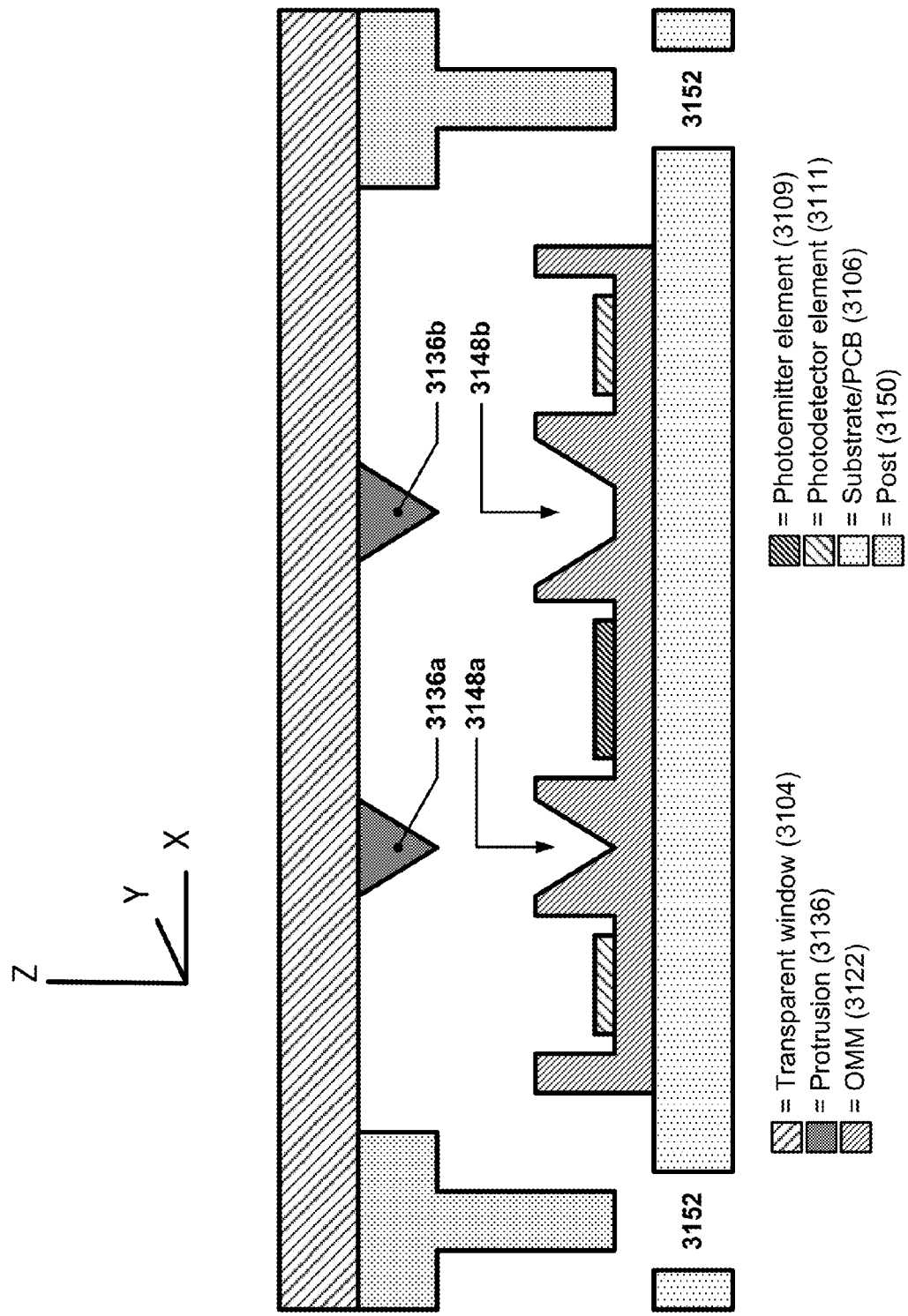
FIG. 31 is a diagram illustrating a configuration of protrusions and wall recesses that may allow for some manufacturing variances, according to an example.

In addition to the various implementations discussed above, the present inventors also conceived of techniques for reducing instances in which a barrier wall recess cannot properly intermesh with a protrusion due to variations in the manufacturing process of the protrusions and/or barrier wall recesses. For example, FIG. 31 is a diagram illustrating a configuration of protrusions and barrier wall recesses that may allow for some manufacturing variances, according to an example. FIG. 31 illustrates an OMM 3122 with a photo-emitter element 3109 and two photodetector elements 3111. Further, the OMM 3122 may include barrier walls that are interposed between the photo-emitter and each photodetector. Consistent with examples discussed above, protrusions 3136 from a transparent window 3104 may intermesh or otherwise interlock with features in a barrier wall, such as recesses, to reduce direct light paths from the photo-emitter to photodetectors.

Figure 32:
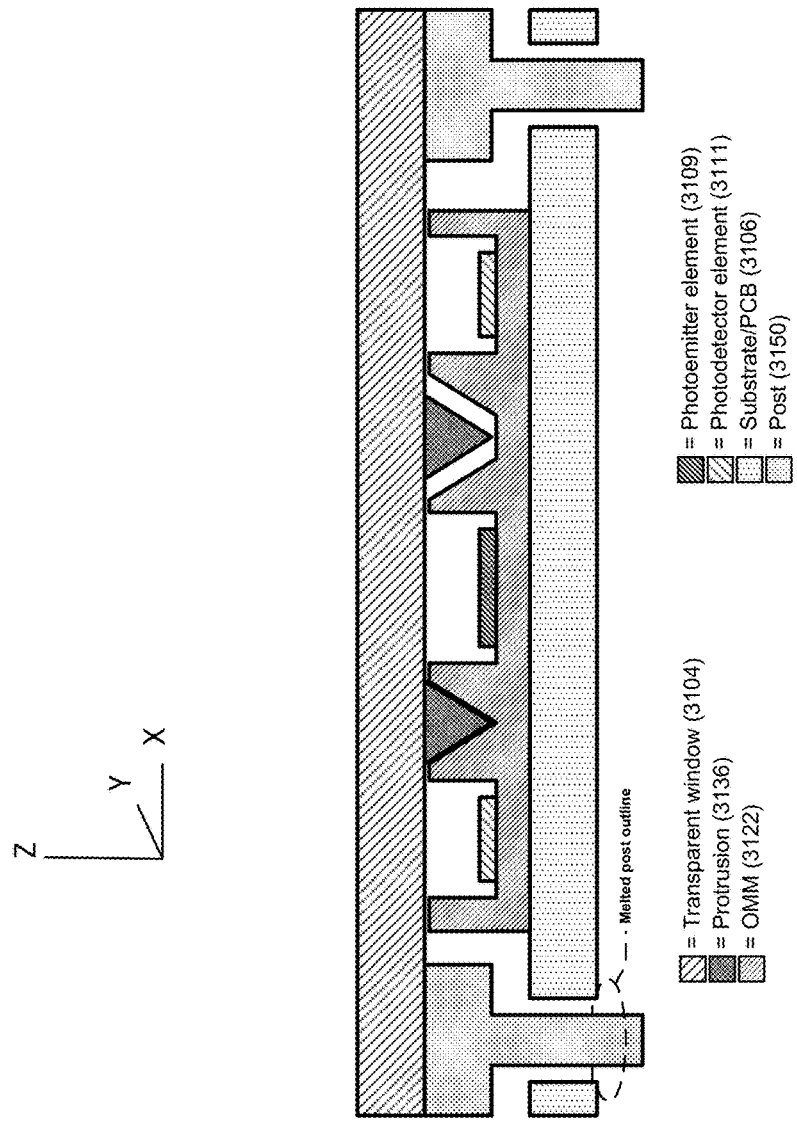
FIG. 32 is a diagram of the configuration of FIG. 31 in an assembled state.

As shown in FIG. 31, the protrusion 3136a may pair or otherwise interlock with a recess 3148a, while the protrusion 3136b may pair or otherwise interlock with a recess 3148b. In some cases, such as that shown in FIG. 31, the shapes of the protrusion 3136a and the recess 3148a may, due to the complementary surface profiles they have, provide relative stability (preventing motion between the transparent window and the OMM to less than a threshold distance, say 0.2 mm) along at least one axis of motion; in the depicted example, motion along the negative Z axis would also be prevented since the window 3104 would rest on the upper surface of the OMM 3122 or both surfaces of the protrusion 3136a would be in contact with both surfaces of the recess 3148a. Such may be the case because the dimensions of the recess 3148a and of the protrusion 3136a result in limited gap distances between each other when the transparent window 3104 is assembled with the OMM 3122, whereby the surfaces of the protrusion 3136a and the recess 3148a make contact and prevent motion along a given axis. For example, FIG. 32 shows that, when assembled, the combination of the protrusion 3136a and the recess 3148a may prevent movement along at least the X axis. It is to be understood that the shapes used by the protrusion 3136a and the recess 3148a may differ from those shown in FIG. 31 and may embody the designs shown elsewhere in this disclosure. Further, in some cases, the dimensions of the recess 3148a may be chosen to accommodate manufacturing variations (which may be referred to herein as a "variation threshold"). By way of example and not limitation, a dimension of the shapes of the protrusion 3136a and the recess 3148a may be selected to accommodate a variation threshold that is around 0.2 mm, although other embodiments may include other variation thresholds, such as a range of variation up to 0.5 mm.

Compared to recess 3148a, recess 3148b may be of a nonconforming shape when compared to the protrusion to which it is designed to be paired (e.g., protrusion 3136b). As used herein, a recess may be of a non-conforming shape when the recess, if intermeshed with the protrusion, does not stabilize the transparent window along one or more axes of motion. Such a situation may occur when the shape of the recess does not match the shape of the protrusion or if the width of the recess is elongated by some threshold amount compared with the corresponding width of the protrusion that interfaces with that recess. Using FIG. 31 as an illustration, the shape of the protrusion 3136b may be of a triangular shape, while the recess 3148b may be of a different shape, such as a trapezoidal shape, as one example. Accordingly, when paired, the combination of the recess 3148b and the protrusion 3136b may exhibit a fair amount of margin (e.g., a space or gap between edges, say greater than some variation threshold (e.g., 0.2 mm in one case)). Because of this margin, the combination of the recess 3148b and the protrusion 3136b may lack the characteristic of stabilizing movement between the transparent window and the OMM seen in the combination of features such as protrusion 3136a and recess 3148a. However, this margin allows for greater variations in the shapes, sizes, and positioning of the protrusions and the recesses, as may occur in the manufacturing and assembly processes. In comparison, the recess 3148a and the protrusion 3136a may be conforming shapes in that they each represent a triangle and the triangles are similar to each other.

The posts 3150 may provide relative stability along a third axis (e.g., the Y axis) of movement when the transparent window and the OMM are assembled together. The posts 3150 may also provide stability along the Z-axis. For example, the posts may be made of plastic and, after passing through corresponding holes 3152 on a substrate or PCB 3106 with the OMM 3122 having the photo-emitter element 3109 and the photodetector elements 3111, the ends of the posts 3150 protruding through the holes 3152 may be melted to form a "mushroom"—the "head" of the mushroomed portion may be in contact with the back face of the substrate 3106, thus preventing movement in the +Z axis direction, as well as with the walls of the holes 3152, thus preventing movement in the Y axis direction and potentially further preventing movement in the X axis direction.

Figure 33:
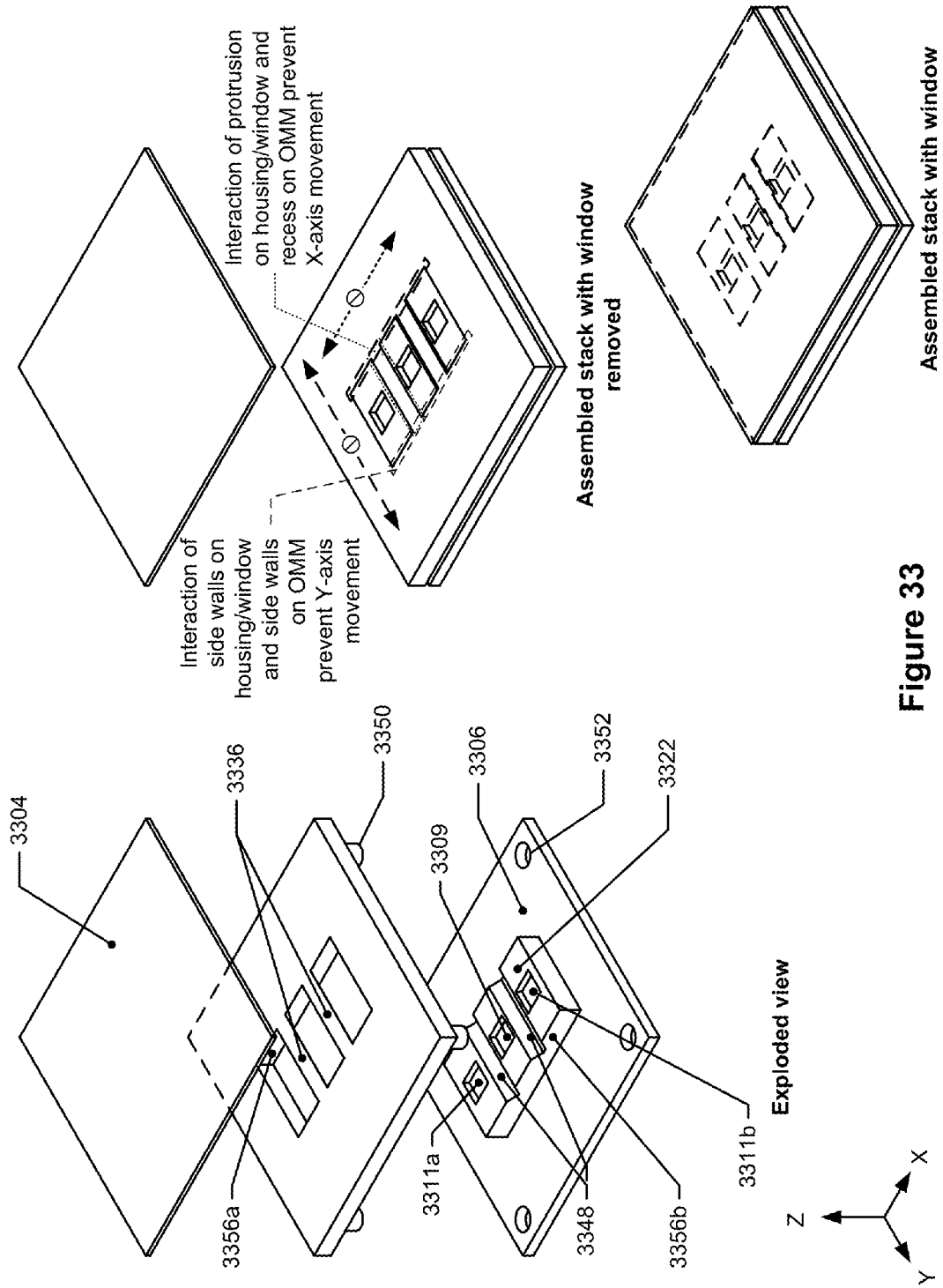
FIG. 33 is a diagram of a configuration similar to that of FIG. 31.

In some implementations, such as that shown in simplified form in FIG. 33, the protrusions and recess(es) may provide relative stability between the OMM and the window in one direction, e.g., perpendicular to the recess groove direction, and the sidewalls of the OMM may interact with sidewalls of the housing/window to provide relative stability in another direction, e.g., parallel to the recess groove direction. Relative stability in the third direction, e.g., normal to the substrate, may be provided by mushrooming the post ends that protrude through the substrate, or by some other mechanism, such as bonding the components together. In FIG. 33, an OMM 3322 is shown mounted to a substrate 3306; the OMM 3322 has a photo-emitter element 3309 and two flanking photodetector elements 3311a, b. The OMM 3322 has two recesses 3348 that extend across the width of the OMM 3322, which may interface with corresponding protrusions 3336 (which may be triangular in cross-section, as with the protrusions 3136 discussed in the above example) to stabilize the window 3304 relative to the OMM 3322 in the X-axis direction. The window 3304 may be bonded to, or co-molded with, the housing structure providing the protrusions 3336 and posts 3350, such that the window 3304, protrusions 3336, and the posts 3350 move as a unit. The posts 3350 may be inserted into holes 3352 and the ends thereof melted, similar to the posts 3150, in order to stabilize the window 3304 in place relative to the OMM 3322 in at least the Z-axis direction. As discussed above, the OMM 3322 may have sidewalls, such as sidewall 3356b, that may interact with corresponding sidewalls, such as sidewall 3356a (sidewalls 3356a and 3356b do not interact with one another, but with corresponding sidewalls that are not visible in this view) in order to stabilize the window 3304 relative to the OMM 3322 in the Y-axis direction.

Figure 34:
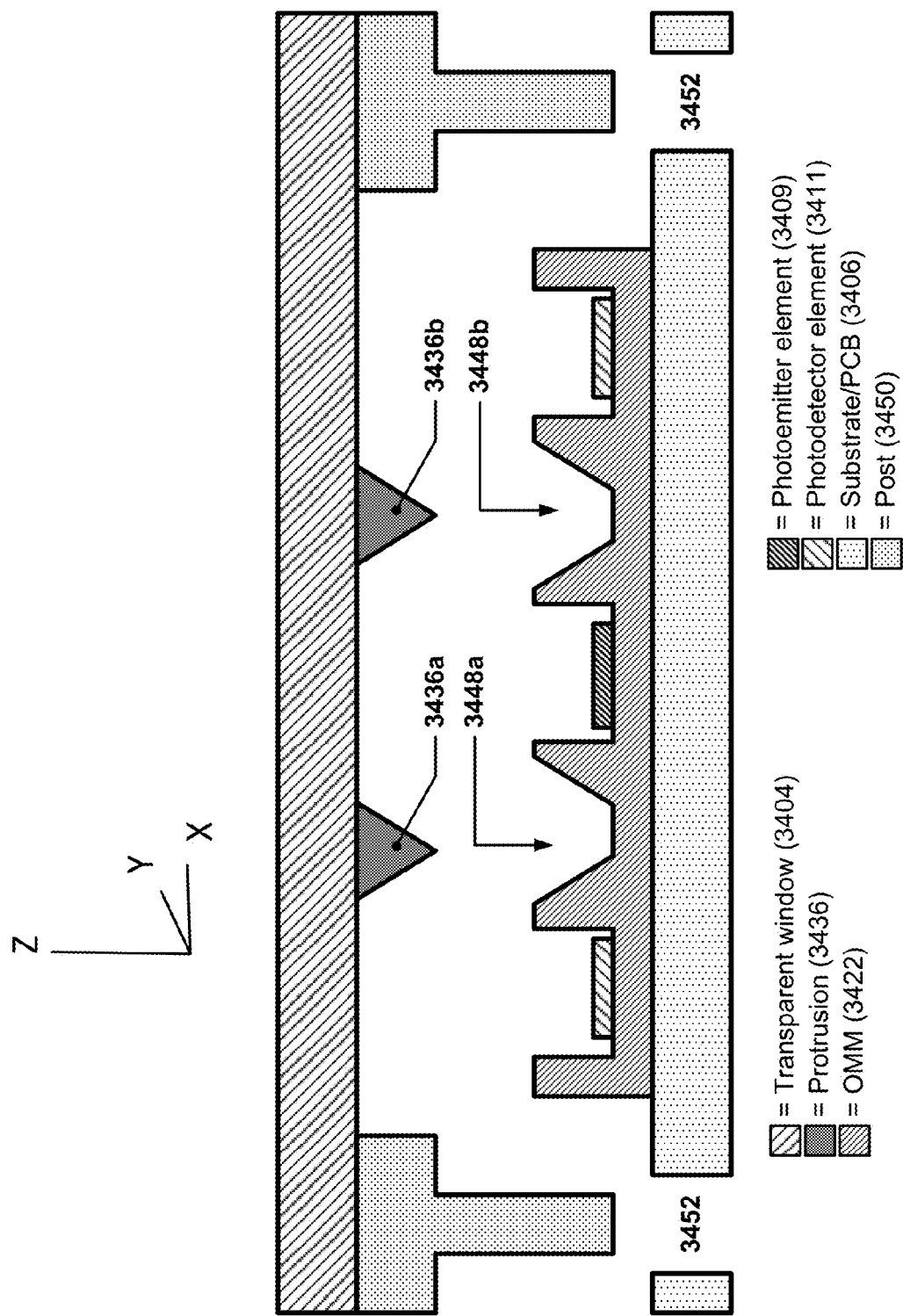
FIG. 34 is a diagram illustrating a different configuration of protrusions and wall recesses that allow for manufacturing variations, in accordance to one example.

In some cases, rather than provide one recess within a barrier wall that includes a nonconforming shape to accommodate manufacturing variations, some embodiments may include multiple recesses, each with a nonconforming shape so that the OMM/transparent window can accommodate even greater manufacturing variations. For example, FIG. 34 is a diagram illustrating a different configuration of protrusions 3436 and barrier wall recesses 3448 that allow for manufacturing variations, in accordance with one example. As shown in FIG. 34, recesses 3448a,b both include nonconforming shapes with respect to protrusions 3436a,b. Because of the nonconforming shapes, when the transparent window is assembled to the OMM, the protrusions, when joined with the recesses, may only stabilize movement along a single axis (e.g., the Z axis) rather than two axes, as may be the case in FIG. 31. To accommodate for this loss of stability, the posts 3406a,b may be inserted in cavities or holes with dimensions that prevent movement, e.g., holes with similar diameters as the posts, along the other two axes of movement, e.g., the X and Y axes.

It is to be understood that the photodetector(s) and photo-emitter(s) of OMMs discussed herein may, in various implementations, all be mounted to a common substrate within the OMM, e.g., a substrate that has the barrier walls discussed herein mounted to it or that is embedded within a molded plastic or resign component that forms the barrier walls discussed herein.

The present inventors have also conceived of OMM configurations that may be particularly useful in certain mixed-mode measurement systems. Optical physiological parameter measurement devices may be engineered to be particularly suited to measuring a particular type of physiological parameter, and thus may have characteristics that make such devices unsuitable for measuring other types of physiological parameters. For example, optical physiological parameter measurement devices that utilize photo-emitter elements that predominantly emit light in the green light spectrum, i.e., where more than 50% of the light intensity of the photo-emitter is at wavelengths within the green light spectrum, may be particularly well-suited to measuring heart rate in a variety of conditions, e.g., even in daylight hours when there is a large amount of ambient background light present. An optical physiological parameter measurement device that utilizes photo-emitter elements in the red or infrared spectrum, however, may be particularly well-suited to measuring SpO2 levels (arterial oxygen saturation). Obtaining both types of physiological measurements with one type of sensor may, however, be undesirable from a performance standpoint. For example, an optical physiological parameter measurement device that uses green light may not be able to accurately detect SpO2 levels, and an optical physiological parameter measurement device that uses red or infrared light may be a poor performer for detecting heart rate, especially in ambient daylight conditions. Thus, it may be desirable to include multiple different types of optical physiological parameter measurement devices in a single OMM in order to provide a wider range of capability. The present inventors have conceived of several such combined-sensor OMM designs that may provide superior performance over existing combined-sensor OMMs.

FIG. 35 depicts a side view diagram of an example OMM with two different types of optical physiological parameter measurement devices. In FIG. 35, an OMM 3522 is depicted that has three or more wells or recesses in it; a transparent window 3504 may be placed atop the OMM 3522—the transparent window 3504 may have protrusions (such as the triangular ones that are depicted) that may interface with corresponding recesses in barrier walls of the OMM 3522, in a manner similar to other implementations discussed herein. A photo-emitter element 3509a, such as an LED that emits light predominantly in the green light spectrum, which may be particularly well-suited to measuring heart rate under a variety of ambient lighting conditions, may be located in a well between two distal wells, e.g., the middle recess or well depicted in this example, and a photodetector element 3511a may be located in an adjoining, distal well. As used herein, a "distal" well or recess is a well or recess that has at least two other wells or recesses located to one side or the other of that well or recess. The photodetector element 3511a may, for example, include a filter 3554a that is selected so as to be transmissive to the light wavelengths emitted by the photo-emitter element 3509a but non-transmissive to other light wavelengths, such as ambient light wavelengths. In some implementations, the filter 3554a may be omitted if such filtering is unnecessary. In addition to the photodetector element 3511a, the same well or recess may also include a photo-emitter element (or elements) 3509b, which may, for example, be a photo-emitter element or photo-emitter elements that emit light primarily in the red and/or infrared light spectrum, which may be useful for measuring physiological parameters such as SpO2. A photodetector element 3511b may be located in another well or recess on an opposite side of OMM 3522 from the well or recess with the photo-emitter element(s) 3509b. Thus, the photo-emitter element 3509a may be interposed between the photo-emitter elements 3509b/photodetector element 3511a and the photodetector element 3511b. Such a configuration causes the distance between the photo-emitter elements 3509b and the photodetector element 3511b to be considerably farther apart than the corresponding distance between the photo-emitter element 3509a and the photodetector element 3511a. Thus, for example, green light from the photo-emitter element 3509a, which may be absorbed more readily than red or infrared light as it diffuses through human tissue, may experience a much shorter path length when transiting from the photo-emitter element 3509a through a person's tissue to the photodetector element 3511a than red or infrared light from the photo-emitter element(s) 3509b as such light transits through the person's tissue to the photodetector element 3511b. Additionally, red and infrared light may be absorbed to a lesser extent by blood than green light—spacing the red and/or infrared photo-emitter element(s) farther from the corresponding photodetector as compared with the green photo-emitter element(s) and corresponding photodetector allows such red and/or infrared light to pass through more blood vessels before reaching the corresponding photodetector, thus providing more opportunity for the light to be modulated by volumetric pulsations in the blood vessels, thereby increasing the signal-to-noise ratio of such a red and/or infrared signal. Discrete photodetector elements 3511a and 3511b may be used to allow each photodetector element 3511a and 3511b to be separately filtered, e.g., by filters 3554a and 3554b, respectively, to exclude light having wavelengths other than the wavelengths of light emitted by the respective photo-emitter elements 3509a and 3509b. This may allow both optical physiological parameter measurement devices to operate concurrently with minimal interference between the two, as well as allow both optical physiological parameter measurement devices to operate with minimal potential interference from ambient light sources. Such filters may optionally be omitted, in some implementations, if, for example, the optical physiological parameter measurement devices are not be operated concurrently or if ambient light conditions are such that such filtering is unnecessary.

FIG. 36 depicts a side view diagram of another example OMM with two different types of optical physiological parameter measurement devices. In FIG. 36, an OMM 3622 is depicted that has three or more wells or recesses in it that are arranged side-by-side. Photo-emitter elements 3609a and 3609b may be located in one of the distal recesses, such as in the depicted configuration. The photo-emitter element 3609a may be an LED that emits light predominantly in the green light spectrum, which may be particularly well-suited to measuring heart rate under a variety of ambient lighting conditions, whereas the photo-emitter element (or elements) 3609b may, for example, be an LED (or LEDs) that emit light primarily in the red and/or infrared light spectrums, which may be useful for measuring physiological parameters such as SpO2.

Corresponding photodetector elements 3611a and 3611b may be located in separate, additional wells or recesses, such as the middle well (for photodetector element 3611a) and the opposing distal well (for photodetector element 3611b). Each of these photodetector elements 3611a and 3611b may optionally be filtered by a separate filter 3654a and 3654B, respectively, similar to the filters in the example of FIG. 35 (it is to be appreciated that similar such optical filters may be used with any of the photodetector elements in any of the implementations discussed herein, if desired). The OMM 3622 discussed above may offer advantages and functionality similar to that described above with respect to the OMM 3522.

In all of the implementations discussed herein, the "well" or "recess" that houses a photo-emitter in an OMM may be coated with, or made from, a reflective material, such as a white material, a mirror or high-reflectivity coating, a metal, or any other suitable smooth, optically reflective material. Such a reflective material may increase the efficiency of the photo-emitter by causing light that might otherwise be absorbed by the OMM structure, e.g., perimeter walls or barrier walls, to instead be reflected out of the OMM and into a person's tissue. According to some embodiments, the wells or recesses of an OMM that house the photodetectors may be made of or incorporate material different from the material used in the wells or recesses that house the photo-emitter(s). Such different material may include black plastic, although they may be any other material, such as reflective material similar to that used in the photo-emitter wells or recesses. In some cases, each well housing the photo-emitter(s) may be in one discrete subcomponent or portion of the OMM and the well (or wells) housing the photodetector(s) may be in another subcomponent or portion of the OMM; these subcomponents or portions may be combined or otherwise joined together to form the OMM. Additionally or alternatively, the reflective material can be applied directly onto the PCB supporting the photo-emitter(s) and the light barrier walls (of various materials) can then be glued to the PCB to separate the photo-emitters from the detectors. In some implementations, the PCB may be dyed or otherwise colored or coated so as to be different colors under the photo-emitter(s), e.g., a white or reflective coating or coloring, and under the photodetectors, e.g., a black or absorptive coating.

Figure 37:
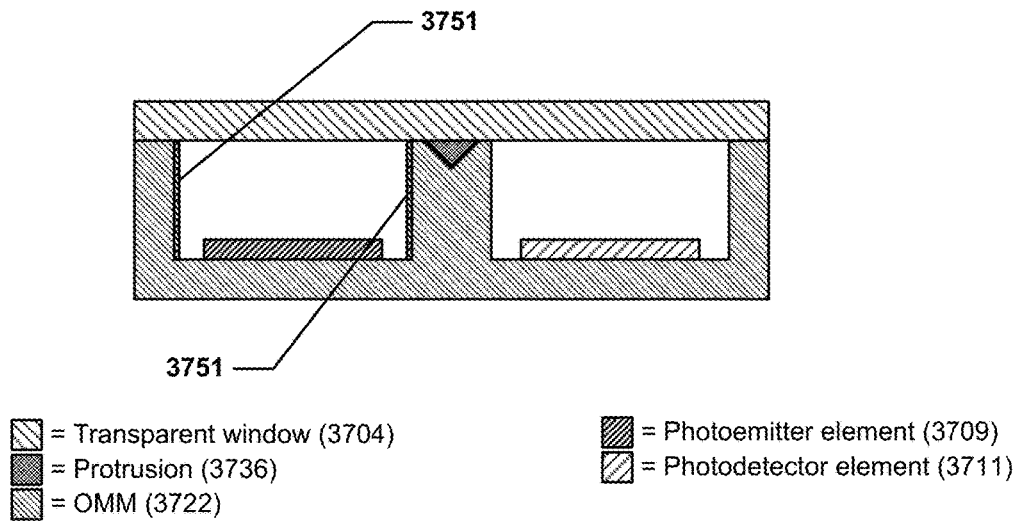
FIG. 37 depicts a side view representation of an example OMM with a reflective coating.

FIG. 37 depicts a side view representation of an example OMM with a reflective coating. In FIG. 37, an OMM 3722 is shown that has a photo-emitter element 3709 and a photodetector element 3711, each of which is located in a different well or recess of the OMM 3722. A window 3704 caps the OMM 3722, and a protrusion 3736 interfaces with a corresponding recess feature in a barrier wall of the OMM 3722 that separates the photo-emitter 3709 and the photodetector 3711. Optically reflective coatings 3751 have been applied to interior walls of the recess having the photo-emitter element 3709.

Figure 38:
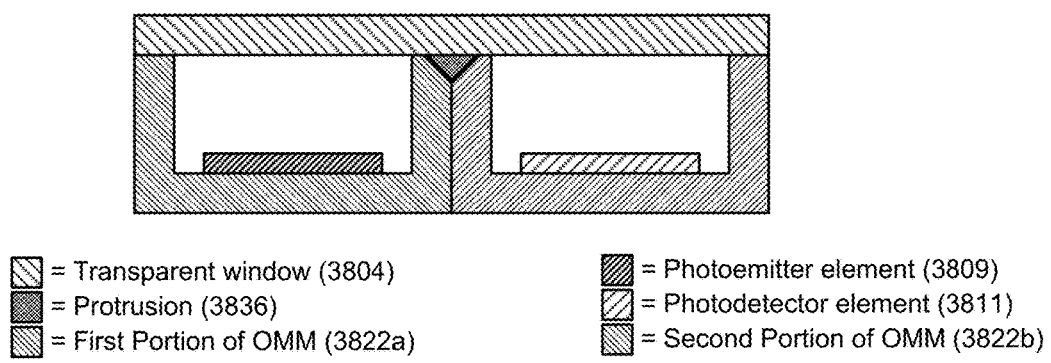
FIG. 38 depicts a side view representation of an example OMM with a reflective portion.

FIG. 38 depicts a side view representation of an example OMM with a reflective well. In FIG. 38, an OMM 3822 is shown that has a photo-emitter element 3809 and a photodetector element 3811, each of which is located in a different well or recess of the OMM 3822. A window 3804 caps the OMM 3822, and a protrusion 3836 interfaces with a corresponding recess feature in a barrier wall of the OMM 3822 that separates the photo-emitter 3809 and the photodetector 3811. The OMM 3822 is formed from two separate components or portions, portions 3822a and 3822b. The photodetector element 3811 is located in the portion 3822b, and the photo-emitter element 3809 is located in the portion 3822a, which may be made, for example, from a white, reflective plastic material. These two portions may be joined together, e.g., via bonding or co-molding, to form the OMM 3822.

Figure 39:
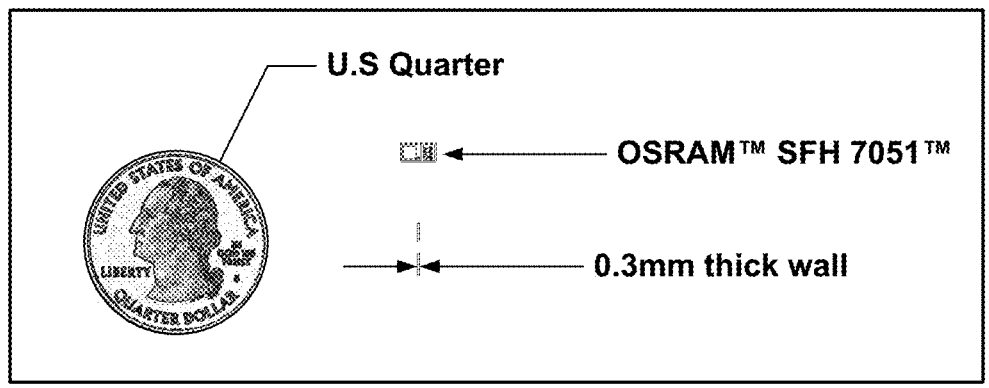
FIG. 39 is a to-scale Figure showing a typical OMM and OMM wall thickness as compared with a U.S. $0.25 coin.

It is to understood that the issues discussed herein regarding tolerance stack-ups in the context of biometric monitoring devices and the potential for light leakage due to such tolerance stack-ups are, generally speaking, issues that were previously generally unknown in the area of optical heart rate sensors, as only recently have such sensors been miniaturized to such an extent. To give some sense of scale as to how small OMMs are, FIG. 39 is a to-scale figure showing a typical OMM, such as an OSRAM™ SFH 7050™, and the barrier wall thickness for such an OMM as compared with a U.S. $0.25 coin. As can be seen, the sizes of these components are truly miniscule.

Generally speaking, the barrier walls and protrusions, as well as the other light-blocking structures discussed herein, may be interposed between the photodetector element and the photo-emitter elements. In most, if not all, implementations, this spatial relationship is with regard to the photo-emitter element or elements that are the closest operable photo-emitter elements to the photodetector element. "Operable" in this case refers to photo-emitter elements that are operated in order to obtain an optical measurement from a person's skin using the photodetector.

It is also to be understood that while the OMMs and optical sensor arrangements discussed herein have typically involve multiple photo-emitter elements and a single photodetector element, the concepts discussed herein may be applied to OMMs or optical sensor arrangements where there are single photo-emitter elements and/or multiple photodetector elements. It is to be further understood that the photo-emitter elements may, as noted earlier, be tuned to emit light in a particular portion of the light spectrum. In some implementations, multiple photo-emitter elements may be used, and two or more of these photo-emitter elements may emit light of different spectra. For example, an OMM may include a green photo-emitter, a yellow photo-emitter, a red photo-emitter, an infrared photo-emitter, or any other suitable photo-emitter. The concepts outlined herein may be used with any variety of different types of photo-emitters.

It is also to be understood that there may be a variety of different barrier wall and protrusion intermeshing surface profiles that, while not explicitly depicted herein, nonetheless embody the concepts discussed herein. These additional surface profiles are to be understood as also falling within the scope of this disclosure. Moreover, it is to be understood that surface profiles similar to the surface profiles explicitly depicted herein but with one or more surfaces that may deviate, for example, ±10° from the angular orientations apparent from the Figures are also explicitly contemplated herein, although it is to be understood that this disclosure is not limited to only such surface profiles.

The photo-emitters discussed herein may include, for example, light-emitting diodes (LEDs), laser diodes, or other light-emitting devices. In cases where a color-specific photo-emitter is used, it is to be understood that such a photo-emitter may emit light with a peak intensity of the color specified and with a spectral line half-width less than or equal to 40 nm. For green photo-emitters, the peak intensity light may be in the 520 to 555 nm wavelength range. For red photo-emitters, the peak intensity light may be in the 640 to 700 nm wavelength range. For infrared photo-emitters, the peak intensity light may be 700 nm or longer in wavelength. It is to be understood that the concepts herein may be applicable to optical physiological sensors utilizing photo-emitters of any of a variety of different emission spectra, including white light emitters as well as color-specific emitters (or combinations of different color-specific emitters).

It is also to be understood that the photo-emitter elements and photodetector elements referred to herein may be discrete photo-emitter and photodetector dies or may be photo-emitter semiconductor packages or photodetector packages. A "die" is a portion of a semiconductor wafer, e.g., an integrated circuit that has been cut or "diced" from a larger semiconductor wafer. Dies are typically extremely compact due to the expense of manufacturing a semiconductor wafer—it is desirable to include as many dies as possible in a wafer to reduce the cost per die. Due to the small size and fragility of dies, however, they are typically packaged in a larger container before being sold to electronics manufacturers. Such containers are referred to as "semiconductor packages," and may, for example, feature a substrate having various electrical interconnects that may be soldered to electrical interconnects on the semiconductor die, e.g., through wire bonding or other connection method. The substrate may have a larger footprint than the die, and larger solder contact pads that facilitate lower-tolerance soldering operations more typically found in PCB assembly manufacturing equipment. The substrate, wiring connections, and die may also be encapsulated in a hard exterior shell, e.g., cured epoxy, to prevent short circuits, damage, etc. to the die and to facilitate handling of the package.

The techniques discussed herein may be applicable to both die-level and package-level photo-emitter and/or photodetector devices, although these techniques may be particularly beneficial in the context of die-level photo-emitter and/or photodetector devices due to the fact that assembly tolerance stack-ups in biometric monitoring devices utilizing die-level photo-emitter and/or photodetector devices, which are much smaller than package-level versions of these devices, are proportionately much larger compared to the photo-emitter and/or photodetector die size than when compared to a photo-emitter and/or photodetector package size. As a result, light leakage may be a more pronounced issue when using OMMs, which integrate the photo-emitter die(s) and photodetector die(s) into one semiconductor package (as compared to using discrete semiconductor packages for the photo-emitters and the the photodetectors that are, generally speaking, much larger than an integrated module).

Importantly, the present invention is neither limited to any single aspect nor implementation, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

What is claimed is:

1. An optical physiological parameter measurement apparatus, comprising:
    an optical measurement module including three or more recessed regions separated from each other by two or more barrier walls, the recessed regions including at least two distal recessed regions and the two or more barrier walls including a first barrier wall that separates at least two of the three or more recessed regions and that includes one or more barrier wall surfaces;
    a window extending over the at least two recessed regions separated by the first barrier wall;
    a protrusion that is attached to or part of the window and that includes one or more protrusion surfaces;
    one or more first photo-emitter elements, the one or more first photo-emitter elements configured to emit light predominantly in a first light spectrum;
    one or more second photo-emitter elements, the one or more second photo-emitter elements configured to emit light predominantly in at least one other light spectrum different than the first light spectrum;
    a first photodetector element; and
    a second photodetector element, wherein:
        the one or more second photo-emitter elements are located in one of the distal recessed regions,
        the second photodetector element is located in one of the other distal recessed regions,
        the first photodetector element is located in one of the recessed regions other than the distal recessed region that the second photodetector element is located in,
        the one or more first photo-emitter elements are located in one of the recessed regions other than the recessed region that the first photodetector element is located in, and
        a subset of the one or more barrier wall surfaces and a subset of the one or more protrusion surfaces define two surface profiles that intermesh with one another between the at least two of the three or more recessed regions.

2. The optical physiological parameter measurement apparatus of claim 1, wherein the first light spectrum is the green light spectrum and the at least one other light spectrum is in the red or infrared spectrum.

3. The optical physiological parameter measurement apparatus of claim 1, further comprising a first optical filter that is positioned so as to filter light received by the first photodetector element, wherein the first optical filter is transmissive to light of the first light spectrum and non-transmissive to light of the at least one other light spectrum.

4. The optical physiological parameter measurement apparatus of claim 1, further comprising a second optical filter that is positioned so as to filter light received by the second photodetector element, wherein the second optical filter is transmissive to light of the second light spectrum and non-transmissive to light of the at least one other light spectrum.

5. The optical physiological parameter measurement apparatus of claim 1, wherein one or more surfaces of one or both of the recessed regions in which the one or more first photo-emitter elements and the one or more second photo-emitter elements are located are reflective.

6. The optical physiological parameter measurement apparatus of claim 5, wherein the one or more surfaces are selected from the group consisting of: white surfaces, mirrored surfaces, or metallic surfaces.

7. The optical physiological parameter measurement apparatus of claim 6, wherein one or more surfaces of one or both of the recessed regions in which the first photodetector element and the second photodetector element are located are made from a different material than the one or more surfaces of the recessed regions in which the one or more first photo-emitter elements and the one or more second photo-emitter elements are located.

8. The optical physiological parameter measurement apparatus of claim 7, wherein the one or more surfaces of the one or both of the recessed regions in which the first photodetector element and the second photodetector element are located are black in color.

9. The optical physiological parameter measurement apparatus of claim 7, wherein:
    the optical measurement module includes at least two discrete sub-components,
    each sub-component includes a different one or more of the recessed regions, and
    at least two of the sub-components are made from materials having different reflective characteristics, and
    the sub-components are joined together to form the optical measurement module.

10. The optical physiological parameter measurement apparatus of claim 1, wherein the first photodetector element is located in the same distal recessed region as the one or more second photo-emitter elements.

11. The optical physiological parameter measurement apparatus of claim 10, wherein the one or more first photo-emitter elements are located in a recessed region between the recessed regions in which the one or more second photo-emitter elements and the second photodetector element are located.

12. The optical physiological parameter measurement apparatus of claim 1, wherein:
    the one or more first photo-emitter elements and the one or more second photo-emitter elements are located in a common one of the recessed regions, and
    the first photodetector element is located in a recessed region in between the recessed regions in which the one or more first photo-emitter elements and the second photodetector element are located.

13. The optical physiological parameter measurement apparatus of claim 1, wherein:
    the window also extends over the first barrier wall.

14. The optical physiological parameter measurement apparatus of claim 1, wherein the two surface profiles defined by the subset of the one or more barrier wall surfaces and the subset of the one or more protrusion surfaces intermesh with one another such that at least a first portion of a barrier wall surface in the subset of the one or more barrier wall surfaces is located closer to the window than at least a first portion of a protrusion surface in the subset of the one or more protrusion surfaces.

15. The optical physiological parameter measurement apparatus of claim 1, wherein at least a second portion of at least one of the one or more barrier wall surfaces is located further from the window than at least a second portion of at least one of the one or more protrusion surfaces.

16. The optical physiological parameter measurement apparatus of claim 1, further comprising a common substrate, wherein:
the first photodetector element, the second photodetector element, the one or more first photo-emitter elements, and the one or more second photo-emitter elements are mounted to the common substrate,
the barrier wall extends away from the common substrate, and
the two surface profiles defined by the subset of the one or more barrier wall surfaces and the subset of the one or more protrusion surfaces intermesh with one another such that:
the barrier wall surfaces in the subset of the one or more barrier wall surfaces face towards the protrusion surfaces in the subset of the one or more protrusion surfaces and the protrusion surfaces in the subset of the one or more protrusion surfaces face towards the barrier wall surfaces in the subset of the one or more barrier wall surfaces,
at least one of the barrier wall surfaces in the subset of the one or more barrier wall surfaces is not parallel to the common substrate, and
at least one of the protrusion surfaces in the subset of the one or more protrusion surfaces is not parallel to the common substrate.

17. The optical physiological parameter measurement apparatus of claim 1, wherein the first photodetector element and the one or more first photo-emitter elements are both mounted to a first side of a common substrate and the barrier wall extends away from the first side of the common substrate.

18. The optical physiological parameter measurement apparatus of claim 1, wherein the protrusion and the first barrier wall are both opaque to at least light in the green wavelength spectrum selected from the group of ranges consisting of: 495 to 570 nm and 500 to 600 nm.

19. The optical physiological parameter measurement apparatus of claim 1, wherein:
the two surface profiles defined by the subset of the one or more barrier wall surfaces and the subset of the one or more protrusion surfaces intermesh with one another such that any optical path originating in one of the recessed regions adjacent to the first barrier wall and reaching the other recessed region adjacent to the first barrier wall by travelling between the two surface profiles must strike at least one surface from the group consisting of the subset of the one or more barrier wall surfaces and the subset of the one or more protrusion surfaces before reaching the photodetector element.

20. The optical physiological parameter measurement apparatus of claim 19, wherein the protrusion and the window are both made from plastic and the protrusion is fused to the window.

21. The optical physiological parameter measurement apparatus of claim 19, wherein an edge of the first photodetector element closest to the one or more first photo-emitter elements is offset from the center of the closest first photo-emitter element by a distance of less than 2.6 mm.

22. The optical physiological parameter measurement apparatus of claim 19, wherein the first barrier wall is less than 1 mm thick as measured along an axis spanning between the first photodetector element and the closest of the one or more first photo-emitter elements.

23. The optical physiological parameter measurement apparatus of claim 19, wherein:
the subset of the one or more barrier wall surfaces includes two barrier wall surfaces forming a first angle between them, and
the subset of one or more protrusion surfaces includes two protrusion surfaces forming a second angle within ±10° of the first angle.

24. The optical physiological parameter measurement apparatus of claim 23, wherein:
the subset of the one or more barrier wall surfaces further includes a third barrier wall surface extending away from one of the two barrier wall surfaces in a direction within ±10° of parallel with the window where the protrusion is located, and
the subset of the one or more protrusion surfaces includes a third protrusion surface extending away from one of the two protrusion surfaces in a direction within ±10° of parallel with the window where the protrusion is located.

25. The optical physiological parameter measurement apparatus of claim 19, wherein the subset of the one or more barrier wall surfaces includes a barrier wall surface that is sloped such that that barrier wall surface approaches the window as that barrier wall surface is traversed from an end of that barrier wall surface closest to the first photodetector element to an end of that barrier wall surface closest to one of the one or more first photo-emitter elements.

26. The optical physiological parameter measurement apparatus of claim 25, wherein the subset of the one or more barrier wall surfaces includes a single barrier wall surface.

27. The optical physiological parameter measurement apparatus of claim 25, wherein the subset of the one or more barrier wall surfaces includes at least two barrier wall surfaces and one of the two barrier wall surfaces extends in a direction within ±10° of parallel with the window where the protrusion is located.

28. The optical physiological parameter measurement apparatus of claim 25, wherein the subset of the one or more barrier wall surfaces includes at least three barrier wall surfaces that are each within ±10° of perpendicular to each adjacent barrier wall surface.

29. The optical physiological parameter measurement apparatus of claim 19, wherein the subset of the one or more barrier wall surfaces and the subset of the one or more protrusion surfaces have complementary profiles.

30. The optical physiological parameter measurement apparatus of claim 19, wherein at least one barrier wall surface in the subset of the one or more barrier wall surfaces is offset from a corresponding protrusion surface in the subset of the one or more protrusion surfaces by between 0 mm and 0.5 mm.

* * * * *